(12) United States Patent
Lee et al.

(10) Patent No.: US 11,563,180 B2
(45) Date of Patent: Jan. 24, 2023

(54) SPIROBIFLUORENE COMPOUND AND PEROVSKITE SOLAR CELL COMPRISING SAME

(71) Applicant: KOREA RESEARCH INSTITUTE OF CHEMICAL TECHNOLOGY, Daejeon (KR)

(72) Inventors: Jaemin Lee, Daejeon (KR); Hye Jin Na, Seoul (KR); Nam Joong Jeon, Gwangju (KR); Jang Won Seo, Seoul (KR); Jun Hong Noh, Daejeon (KR); Tae Youl Yang, Daejeon (KR); Sang Il Seok, Daejeon (KR)

(73) Assignee: KOREA RESEARCH INSTITUTE OF CHECMICAL TECHNOLOGY, Daejeon (KR)

( * ) Notice: Subject to any disclaimer, the term of this patent is extended or adjusted under 35 U.S.C. 154(b) by 14 days.

(21) Appl. No.: 16/348,861

(22) PCT Filed: Nov. 8, 2017

(86) PCT No.: PCT/KR2017/012601
§ 371 (c)(1),
(2) Date: May 9, 2019

(87) PCT Pub. No.: WO2018/088797
PCT Pub. Date: May 17, 2018

(65) Prior Publication Data
US 2019/0288207 A1 Sep. 19, 2019

(30) Foreign Application Priority Data
Nov. 9, 2016 (KR) .......................... 10-2016-0148742

(51) Int. Cl.
| | | |
|---|---|---|
| *H01L 51/00* | (2006.01) | |
| *C07C 213/08* | (2006.01) | |
| *C07C 217/92* | (2006.01) | |
| *C07C 217/94* | (2006.01) | |
| *H01G 9/20* | (2006.01) | |
| *H01L 51/42* | (2006.01) | |

(52) U.S. Cl.
CPC .......... *H01L 51/006* (2013.01); *C07C 213/08* (2013.01); *C07C 217/92* (2013.01); *C07C 217/94* (2013.01); *H01G 9/2009* (2013.01); *H01L 51/0003* (2013.01); *H01L 51/0077* (2013.01); *H01L 51/42* (2013.01); *H01L 51/4253* (2013.01); *C07C 2603/18* (2017.05); *C07C 2603/94* (2017.05); *C07C 2603/97* (2017.05); *H01L 51/0056* (2013.01); *H01L 51/0058* (2013.01); *Y02E 10/549* (2013.01)

(58) Field of Classification Search
CPC .................. H01L 51/006; H01L 51/42; H01L 51/0003; H01L 51/0077; H01L 51/4253; H01L 51/0056; H01L 51/0058; H01L 51/4226; H01G 9/2009; C07C 213/08; C07C 217/92; C07C 217/94; C07C 2603/94; C07C 2603/97; C07C 2603/18; Y02P 70/50; Y02E 10/542; Y02E 10/549
See application file for complete search history.

(56) References Cited

U.S. PATENT DOCUMENTS

| | | | |
|---|---|---|---|
| 2007/0077450 A1* | 4/2007 | Yen ...................... | H01L 51/006 428/690 |
| 2011/0232763 A1 | 9/2011 | Kang et al. | |
| 2015/0065730 A1* | 3/2015 | Montenegro ........ | C07D 209/86 548/440 |
| 2018/0122587 A1* | 5/2018 | Satou ................... | H01G 9/2077 |

FOREIGN PATENT DOCUMENTS

| | | | | |
|---|---|---|---|---|
| JP | 2011-082507 A | 4/2011 | | |
| JP | 2011-113649 A | 6/2011 | | |
| JP | 2012-023266 A | 2/2012 | | |
| KR | 10-2015-0047623 A | 5/2015 | | |
| KR | 10-1608281 B1 | 4/2016 | | |
| WO | WO-2014037847 A2 * | 3/2014 | ......... | H01L 51/0058 |
| WO | 2014/170839 A2 | 10/2014 | | |
| WO | 2016/078738 A1 | 5/2016 | | |

OTHER PUBLICATIONS

Jeon, o-Methoxy Substituents in Spiro-OMeTAD for Efficient Inorganic-Organic Hybrid Perovskite Solar Cells, J. Am. Chem. Soc. 2014, 136, 7837-7840 (Year: 2014).*
International Search Report of PCT Patent Application No. PCT/KR2017/012601, which is parent—6 pages (dated Feb. 9, 2018).
Malinauskas et al., "Enhancing Thermal Stability and Lifetime of Solid-State Dye-Sensitized Solar Cells via Molecular Engineering of the Hole-Transporting Material Spiro-OMeTAD", ACS Applied Materials & Interfaces, vol. 7—11 pages (2015).
Burschka et al., "Sequential deposition as a route to high-performance perovskite-sensitized solar cells", Nature, vol. 499—5 pages (Jul. 18, 2013).
Office Action of corresponding Korean Patent Application No. 10-2017-0148095—7 pages (dated May 7, 2019).

* cited by examiner

*Primary Examiner* — Devina Pillay
(74) *Attorney, Agent, or Firm* — Knobbe, Martens, Olson & Bear LLP

(57) ABSTRACT

A spirobifluorene compound and a perovskite solar cell including the spirobifluorene compound are disclosed. More particularly, a spirobifluorene compound which can be used as a hole transport material of a perovskite solar cell is disclosed. A perovskite solar cell including the spirobifluorene compound as a hole transport material is further disclosed.

3 Claims, No Drawings

SPIROBIFLUORENE COMPOUND AND PEROVSKITE SOLAR CELL COMPRISING SAME

TECHNICAL FIELD

The present invention relates to a spirobifluorene compound and a perovskite solar cell including the same, and more particularly, to a spirobifluorene compound used as a hole transport compound of a perovskite solar cell and a perovskite solar cell including the same.

BACKGROUND ART

In order to solve the problems of depletion of fossil energy and global environmental issues due to the use thereof, research on a recyclable and clean alternative source of energy such as solar energy, wind power, and water power, has been actively conducted.

Among them, interest on a solar cell which directly changes energy from sunlight to electric energy is significantly growing. Here, the solar cell refers to a battery producing current-voltage using a photovoltaic effect which absorbs light energy from sunlight to generate electrons and holes.

Currently, it is possible to manufacture an n-p diode-type silicon (Si) single crystal-based solar cell having light energy conversion efficiency over 20%, which is actually used for solar power generation, and there is a solar cell using a compound semiconductor such as gallium arsenide (GaAs) which has better conversion efficiency than the solar cell based on an n-p diode-type silicon single crystal.

However, since the inorganic semiconductor-based solar cell needs a very highly purified material for higher efficiency, much energy is consumed in purification of raw materials, and expensive process equipment is required for a process of producing a single crystal or thin film using the raw materials, and thus, there is a limitation on lowering the manufacturing cost of the solar cell, which becomes an obstacle to large-scale utilization.

Accordingly, in order to manufacture the solar cell at low cost, costs of the materials used as a core in a solar cell or a manufacturing process need to be greatly reduced, and as an alternative to the inorganic semiconductor-based solar cell, a dye-sensitized solar cell and an organic solar cell which may be manufactured by low cost materials and processes are actively studied.

The organic solar cell allows a simple manufacturing process of elements as compared with the conventional solar cells due to easy processability, versatility, and low unit price of the organic materials, thereby realizing lower manufacturing unit price than that of the conventional solar cells. However, in the case of the organic solar cell, the structure of BHJ is deteriorated by moisture or oxygen in the air to rapidly lower the efficiency, that is, there is a big problem in stability of the solar cell, and when a complete sealing technique is introduced as a method for solving the problem, stability is increased but the price rises.

Meanwhile, a perovskite solar cell, specifically a lead halide perovskite solar cell, has been significantly developed for several years, due to a photoactive layer made of perovskite materials having excellent characteristics, and as a result, currently has efficiency up to 21%, and in order to solve the problems of the organic solar cell as mentioned above, a study to apply Spiro-OMeTAD to the perovskite solar cell also to achieve high efficiency (J. Burschka, N. Pellet, S.-J. Moon, R. Humphry-Baker, P. Gao, M. K. Nazeeruddin and M. Gratzel, *Nature,* 2013, 499, 316-319) has been conducted.

However, satisfactory efficiency to be commercialized has yet to be obtained, and a high-efficiency solar cell is still required.

DISCLOSURE

Technical Problem

An object of the present invention is to provide a spirobifluorene compound which may be used as a hole transport compound of a solar cell, in particular, a high-efficiency inorganic/organic hybrid perovskite solar cell.

Further, another object of the present invention is to provide a perovskite solar cell including the spirobifluorene compound of the present invention.

Technical Solution

The present invention provides a spirobifluorene compound which may be used as a hole transport material of a high-efficiency inorganic/organic hybrid perovskite solar cell, and in one general aspect, the spirobifluorene compound of the present invention is represented by the following Chemical Formula 1:

[Chemical Formula 1]

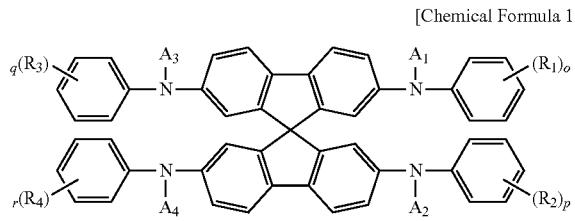

wherein $R_1$ to $R_4$ are independently of one another (C1-C10)alkyl, (C1-C10)alkoxy, (C6-C12)aryloxy, (C6-C12)arylthio, or (C1-C10)alkylthio;

o, p, q, and r are independently of one another an integer of 1 to 5;

$A_1$ to $A_4$ are independently of one another

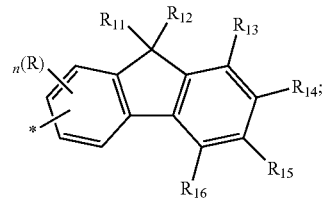

$R_{11}$ and $R_{12}$ are independently of each other hydrogen, (C1-C20)alkyl, (C6-C20)aryl, (C3-C20)heteroaryl, (C1-C20)alkoxy(C1-C20)alkyl, or (C6-C20)aryl(C1-C20)alkyl, or $R_{11}$ and $R_{12}$ are linked to each other to form an aromatic ring-fused spirocycle;

$R_{13}$ to $R_{16}$ are independently of one another hydrogen, (C1-C10)alkyl, (C1-C10)alkylthio, or (C1-C7)alkoxy;

R is (C1-C10)alkyl, (C1-C10)alkylthio, or (C1-C10)alkoxy; and n is 0 or an integer of 1 to 3.

Preferably, in Chemical Formula 1 according to an exemplary embodiment of the present invention, $R_1$ to $R_4$ may be independently of one another (C1-C10)alkoxy, (C6-C12)aryloxy, or (C6-C12)arylthio.

Preferably, in Chemical Formula 1, $R_{11}$ and $R_{12}$ may be independently of each other hydrogen, (C1-C20)alkyl, (C6-C20)aryl, or (C3-C20)heteroaryl, or $R_{11}$ and $R_{12}$ may be linked to each other to form an aromatic ring-fused spirocycle; $R_{13}$ to $R_{16}$ may be independently of each other (C1-C10)alkyl or (C1-C10)alkoxy; R may be (C1-C10)alkyl or (C1-C10)alkoxy; and n may be 0 or an integer of 1 to 3.

More preferably, Chemical Formula 1 may be represented by the following Chemical Formula 2 or 3:

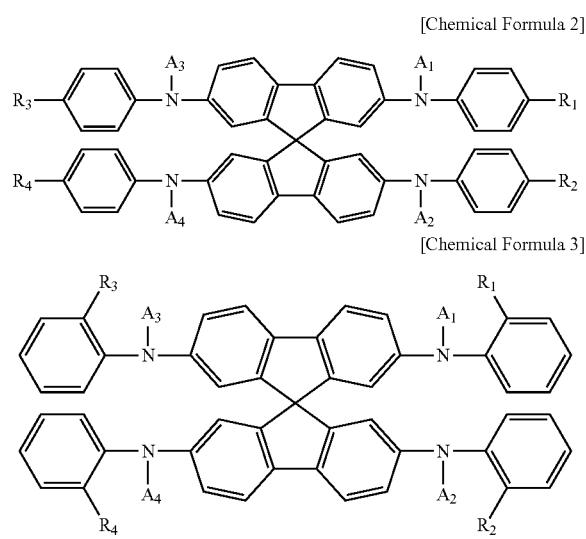

[Chemical Formula 2]

[Chemical Formula 3]

wherein $R_1$ to $R_4$ are independently of one another (C1-C10)alkyl, (C1-C10)alkoxy, (C6-C12)aryloxy, (C6-C12)arylthio, or (C1-C10)alkylthio;

$A_1$ to $A_4$ are independently of one another

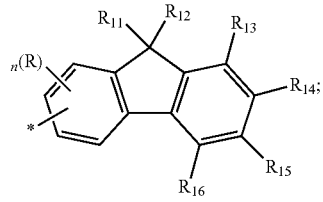

$R_{11}$ and $R_{12}$ are independently of each other hydrogen, (C1-C20)alkyl, (C6-C20)aryl, (C3-C20)heteroaryl, (C1-C20)alkoxy(C1-C20)alkyl, or (C6-C20)aryl(C1-C20)alkyl, or $R_{11}$ and $R_{12}$ are linked to each other to form an aromatic ring-fused spirocycle;

$R_{13}$ to $R_{16}$ are independently of one another hydrogen, (C1-C10)alkyl, (C1-C10)alkylthio, or (C1-C7)alkoxy;

R is (C1-C10)alkyl, (C1-C10)alkylthio, or (C1-C10)alkoxy; and n is 0 or an integer of 1 to 3.

Preferably, in Chemical Formulae 2 and 3 according to an exemplary embodiment of the present invention, $R_1$ to $R_4$ may be independently of one another (C1-C10)alkoxy, (C6-C12)aryloxy, or (C6-C12)arylthio; $R_{11}$ and $R_{12}$ may be independently of each other (C1-C20)alkyl, (C6-C20)aryl, or (C3-C20)heteroaryl, or $R_{11}$ and $R_{12}$ may be linked to each other to form an aromatic ring-fused spirocycle; $R_{13}$ to $R_{16}$ may be independently of one another hydrogen, (C1-C10) alkyl, (C1-C10)alkylthio, or (C1-C7)alkoxy; and n may be 0.

More preferably, in Chemical Formulae 2 and 3 according to an exemplary embodiment of the present invention, $R_1$ to $R_4$ may be independently of one another (C1-C10)alkoxy or (C6-C12)aryloxy; $R_{11}$ and $R_{12}$ may be independently of each other (C1-C20)alkyl or (C6-C20)aryl, or $R_{11}$ and $R_{12}$ may be linked to each other to form an aromatic ring-fused spirocycle; and $R_{13}$ to $R_{16}$ may be independently of one another hydrogen or (C1-C7)alkoxy.

Specifically, the spirobifluorene compound according to an exemplary embodiment of the present invention may be selected from the following compounds, but not limited thereto:

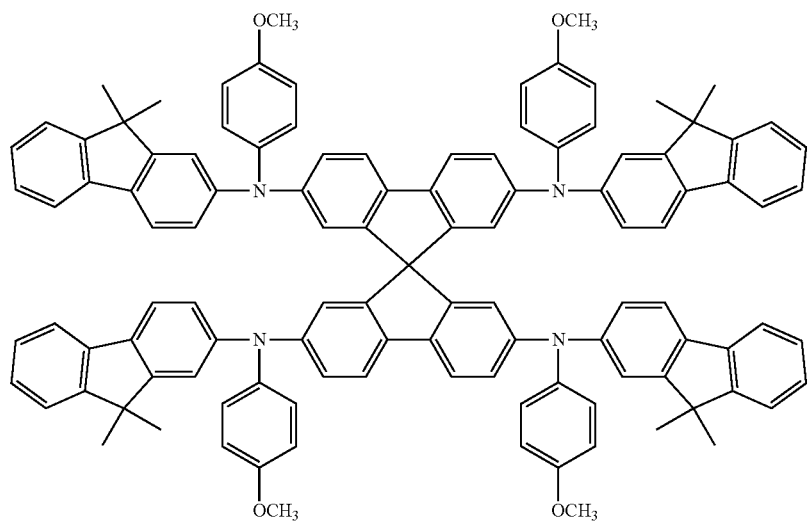

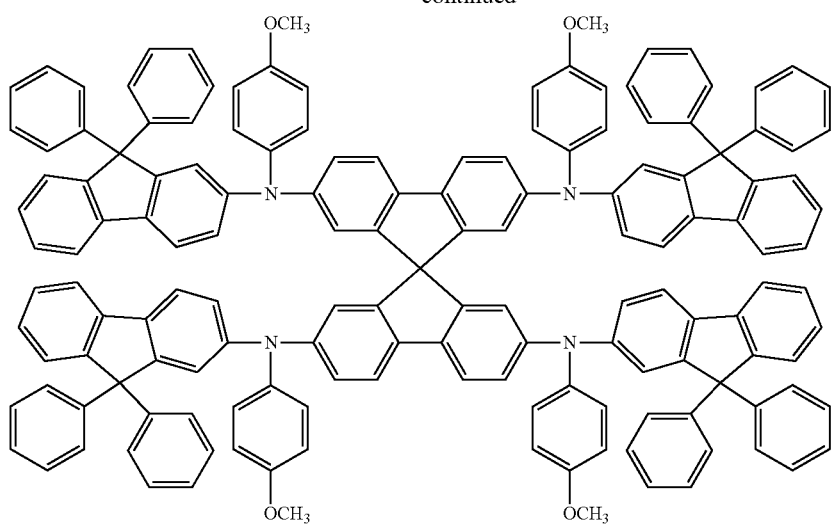
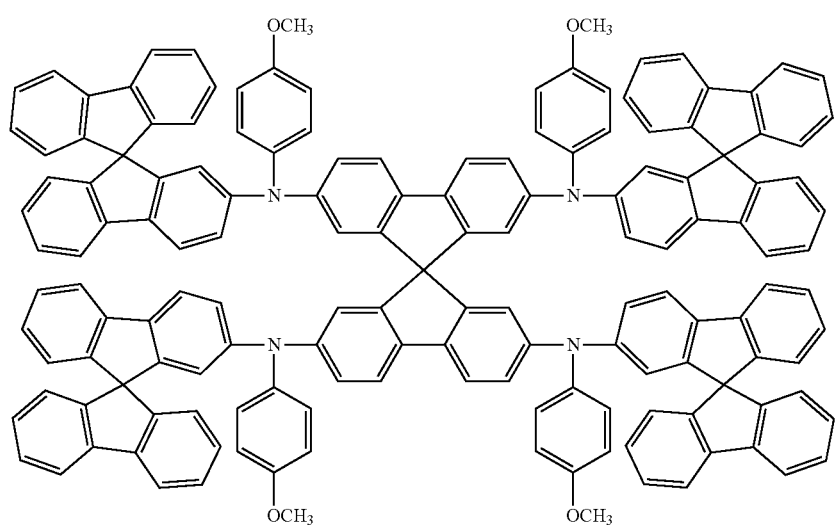
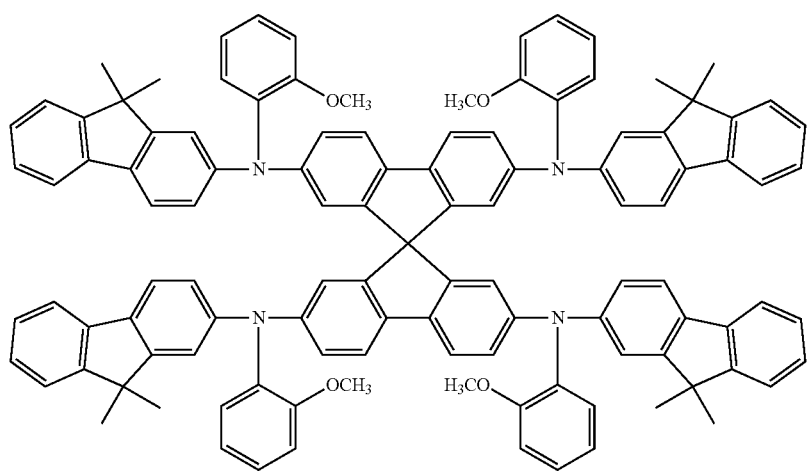

-continued

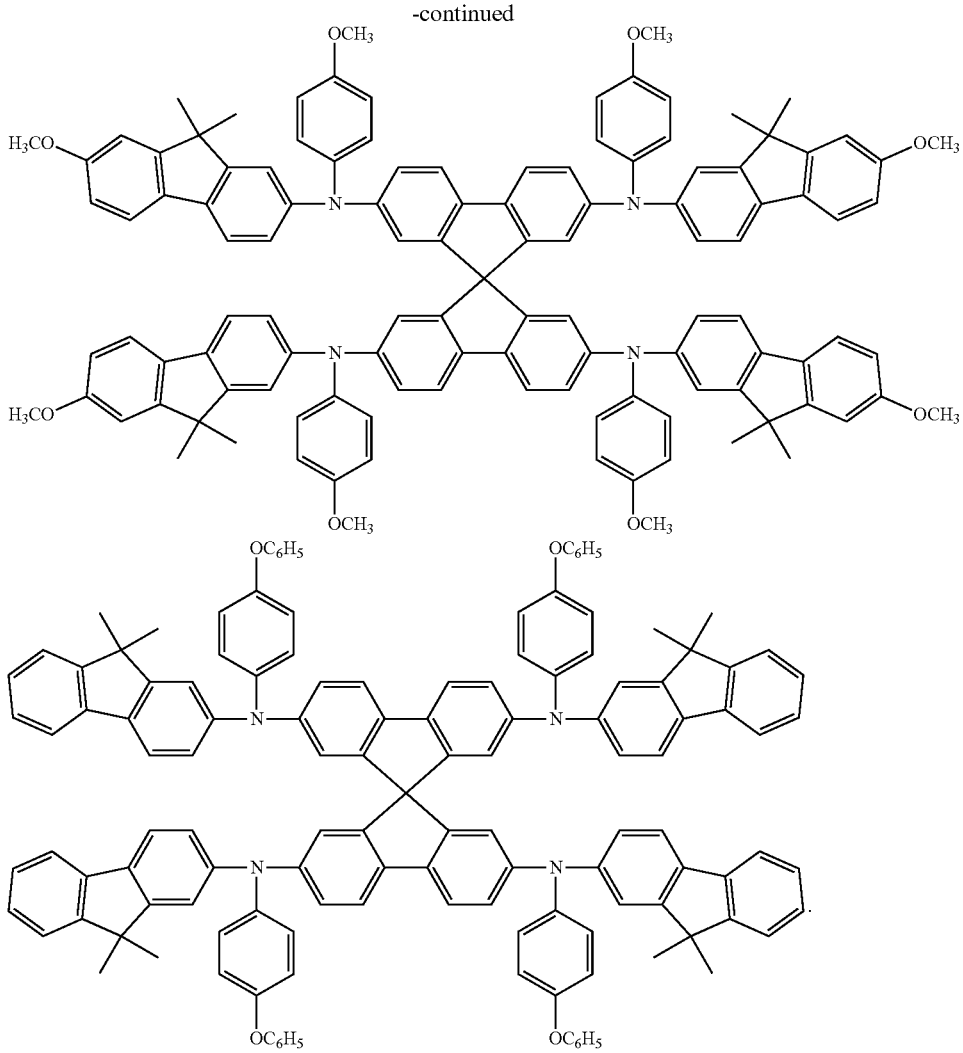

In addition, the present invention provides a perovskite solar cell including the spirobifluorene compound of the present invention.

Preferably, the spirobifluorene compound of the present invention may be used as a hole transport material of a perovskite solar cell.

Preferably, the perovskite solar cell of the present invention may include a first electrode, an electron transport layer formed on the first electrode, a light absorption layer including a compound having a perovskite structure formed on the electron transport layer, a hole transport layer including a spirobifluorene compound represented by Chemical Formula 1, formed on the light absorption layer, and a second electrode formed on the hole transport layer.

Preferably, the hole transport layer of the present invention may be formed by solution-casting a hole transport material including the spirobifluorene compound represented by Chemical Formula 1.

Advantageous Effects

The spirobifluorene compound represented by Chemical Formula 1 of the present invention is used as the hole transport material of the inorganic/organic hybrid perovskite solar cell, thereby having significant improved efficiency as compared with conventional Spiro-OMeTAD.

Furthermore, the spirobifluorene compound represented by Chemical Formula 1 of the present invention is a mono-molecule, and unlike the conventional high molecular hole transport compound, may be prepared by a simple process and easily separated, thereby being very easily commercialized, and has high purity, thereby improving efficiency and durability of the perovskite solar cell adopting the spirobifluorene compound.

In addition, the inorganic/organic hybrid perovskite-based solar cell including the spirobifluorene compound represented by Chemical Formula 1 of the present invention has high electricity generation efficiency and excellent stability, and may be manufactured by a simple solution coating method.

Accordingly, the inorganic/organic hybrid perovskite-based solar cell may be mass-produced within a short time at low cost, thereby increasing a commercialization level of a solar cell.

BEST MODE

Hereinafter, a spirobifluorene compound of the present invention and a perovskite solar cell adopting the same will be described in detail. Technical terms and scientific terms used herein have the general meaning understood by those skilled in the art to which the present invention pertains unless otherwise defined, and a description for the known function and configuration unnecessarily obscuring the gist of the present invention will be omitted in the following description and the accompanying drawings.

The present invention provides a spirobifluorene compound represented by the following Chemical Formula 1:

[Chemical Formula 1]

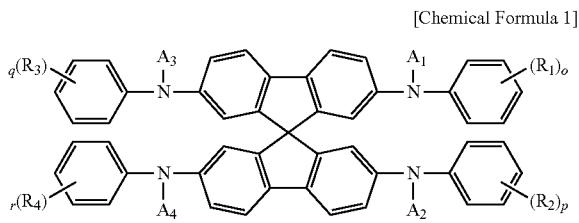

wherein
$R_1$ to $R_4$ are independently of one another (C1-C10)alkyl, (C1-C10)alkoxy, (C6-C12)aryloxy, (C6-C12)arylthio, or (C1-C10)alkylthio;

o, p, q, and r are independently of one another an integer of 1 to 5;

$A_1$ to $A_4$ are independently of one another

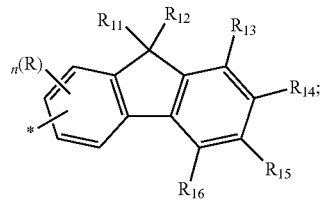

$R_{11}$ and $R_{12}$ are independently of each other hydrogen, (C1-C20)alkyl, (C6-C20)aryl, (C3-C20)heteroaryl, (C1-C20)alkoxy(C1-C20)alkyl, or (C6-C20)aryl(C1-C20)alkyl, or $R_{11}$ and $R_{12}$ are linked to each other to form an aromatic ring-fused spirocycle;

$R_{13}$ to $R_{16}$ are independently of one another hydrogen, (C1-C10)alkyl, (C1-C10)alkylthio, or (C1-C7)alkoxy;

R is (C1-C10)alkyl, (C1-C10)alkylthio, or (C1-C10)alkoxy; and n is 0 or an integer of 1 to 3.

The spirobifluorene compound represented by Chemical Formula 1 of the present invention is used as a hole transport material of a solar cell, in particular a perovskite solar cell, thereby extremely improving efficiency and thermal resistance of a perovskite solar cell adopting the spirobifluorene compound.

The spirobifluorene compound represented by Chemical Formula 1 of the present invention necessarily has four amino groups substituted with a fluorenyl group and a phenyl group in a spirobifluorene main backbone, thereby improving efficiency and durability of the perovskite solar cell adopting the spirobifluorene compound.

Specifically, while the following conventional Spiro-OMeTAD has amino groups all substituted with a phenyl group, the spirobifluorene compound of the present invention has amino groups substituted with phenyl and fluorenyl as the substituent.

Accordingly, the spirobifluorene compound of the present invention has four amino groups substituted with a fluorenyl group, whereby the perovskite solar cell adopting the spirobifluorene compound of the present invention has significantly improved efficiency as compared with the spirobifluorene compound having only one to three amino groups substituted with a fluorenyl group.

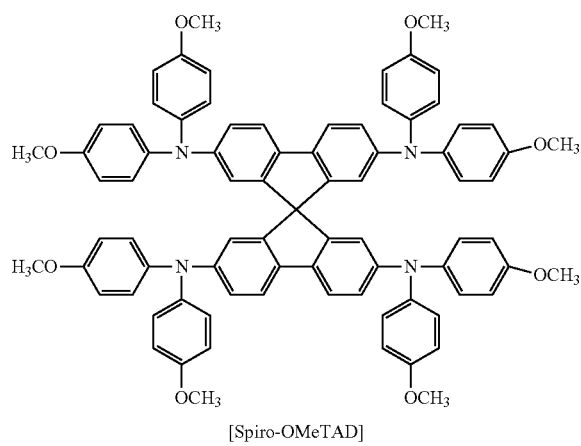 [SMILES: COc1ccc(N(c2ccc(OC)cc2)c2ccc3c(c2)C2(c4cc(N(c5ccc(OC)cc5)c5ccc(OC)cc5)ccc4-3)c3cc(N(c4ccc(OC)cc4)c4ccc(OC)cc4)ccc3-c3ccc(N(c4ccc(OC)cc4)c4ccc(OC)cc4)cc32)cc1]

[Spiro-OMeTAD]

In addition, the spirobifluorene compound of the present invention is a monomolecule, and unlike the conventional high molecular hole transport compound, may be easily synthesized and separated, has a high yield to be very advantageous for commercialization, and also has high purity, thereby extremely improving the efficiency of the perovskite solar cell adopting the spirobifluorene compound.

Preferably, in Chemical Formula 1 according to an exemplary embodiment of the present invention, $R_1$ to $R_4$ may be independently of one another (C6-C12)aryloxy, (C6-C12)arylthio, or (C1-C10)alkoxy.

In terms of obtaining high thermal resistance and high efficiency, preferably, in Chemical Formula 1, $R_{11}$ and $R_{12}$ may be independently of each other hydrogen, (C1-C20)alkyl, (C6-C20)aryl, or (C3-C20)heteroaryl, or $R_{11}$ and $R_{12}$ may be linked to each other to form an aromatic ring-fused spirocycle; $R_{13}$ to $R_{16}$ may be independently of one another (C1-C10)alkyl or (C1-C10)alkoxy; R may be (C1-C10)alkyl or (C1-C10)alkoxy; and n may be 0 or an integer of 1 to 3.

Preferably, Chemical Formula 1 may be represented by the following Chemical Formula 2 or 3:

[Chemical Formula 2]

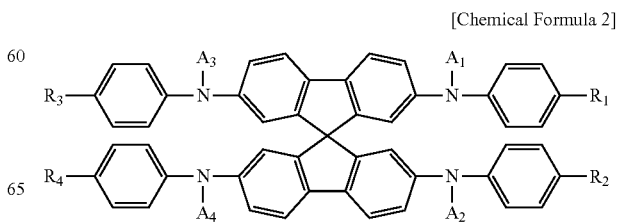

[Chemical Formula 3]

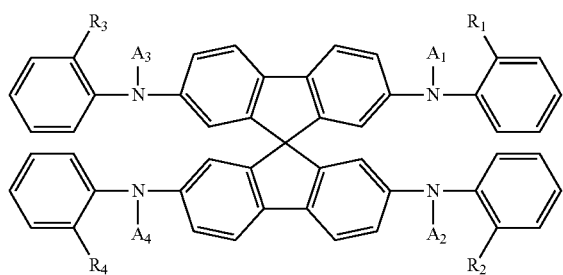

wherein $R_1$ to $R_4$ are independently of one another (C1-C10)alkyl, (C1-C10)alkoxy, (C6-C12)aryloxy, (C6-C12)arylthio, or (C1-C10)alkylthio;

$A_1$ to $A_4$ are independently of one another

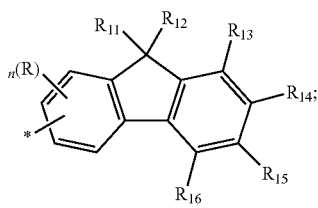

$R_{11}$ and $R_{12}$ are independently of each other hydrogen, (C1-C20)alkyl, (C6-C20)aryl, (C3-C20)heteroaryl, (C1-C20)alkoxy(C1-C20)alkyl, or (C6-C20)aryl(C1-C20)alkyl, or $R_{11}$ and $R_{12}$ are linked to each other to form an aromatic ring-fused spirocycle;

$R_{13}$ to $R_{16}$ are independently of one another hydrogen, (C1-C10)alkyl, (C1-C10)alkylthio, or (C1-C7)alkoxy;

R is (C1-C10)alkyl, (C1-C10)alkylthio, or (C1-C10)alkoxy; and n is 0 or an integer of 1 to 3.

In Chemical Formulae 2 and 3 according to an exemplary embodiment of the present invention, in terms of electricity generation efficiency, preferably, $R_1$ to $R_4$ may be independently of one another (C1-C10)alkoxy, (C6-C12)aryloxy, (C6-C12)arylthio, or (C1-C10)alkylthio; $R_{11}$ and $R_{12}$ may be independently of each other (C1-C20)alkyl, (C6-C20)aryl, or (C3-C20)heteroaryl, or $R_{11}$ and $R_{12}$ may be linked to each other to form an aromatic ring-fused spirocycle; $R_{13}$ to $R_{16}$ may be hydrogen, (C1-C10)alkyl, (C1-C10)alkylthio, or (C1-C7)alkoxy; n may be 0, and more preferably $R_1$ to $R_4$ may be independently of one another (C1-C10)alkoxy or (C6-C12)aryloxy; $R_{11}$ and $R_{12}$ may be independently of each other (C1-C20)alkyl or (C6-C20)aryl, or $R_{11}$ and $R_{12}$ may be linked to each other to form an aromatic ring-fused spirocycle; $R_{13}$ to $R_{16}$ may be hydrogen, (C1-C10)alkylthio, or (C1-C7)alkoxy.

In terms of obtaining excellent efficiency, more preferably, in Chemical Formulae 2 and 3 according to an exemplary embodiment of the present invention, $R_1$ to $R_4$ may be independently of one another (C1-C10)alkoxy or (C6-C12)aryloxy; $R_{11}$ and $R_{12}$ may be independently of each other (C1-C20)alkyl or (C6-C20)aryl, or $R_{11}$ and $R_{12}$ may be linked to each other to form an aromatic ring-fused spirocycle; and $R_{13}$ to $R_{16}$ may be independently of one another hydrogen or (C1-C7)alkoxy.

Specifically, the spirobifluorene compound according to an exemplary embodiment of the present invention may be selected from the following compounds, but not limited thereto:

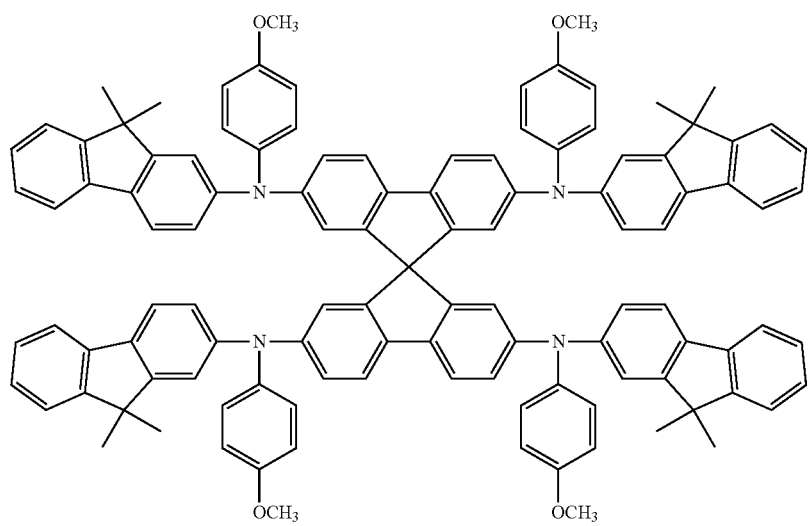

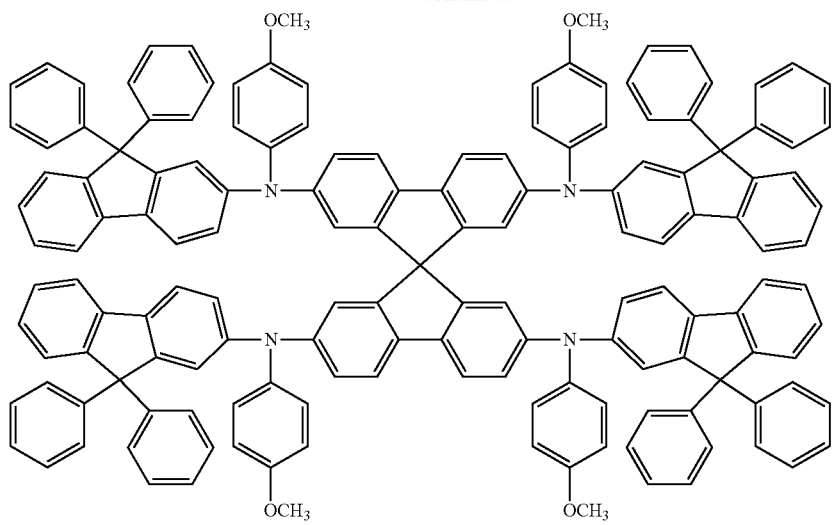
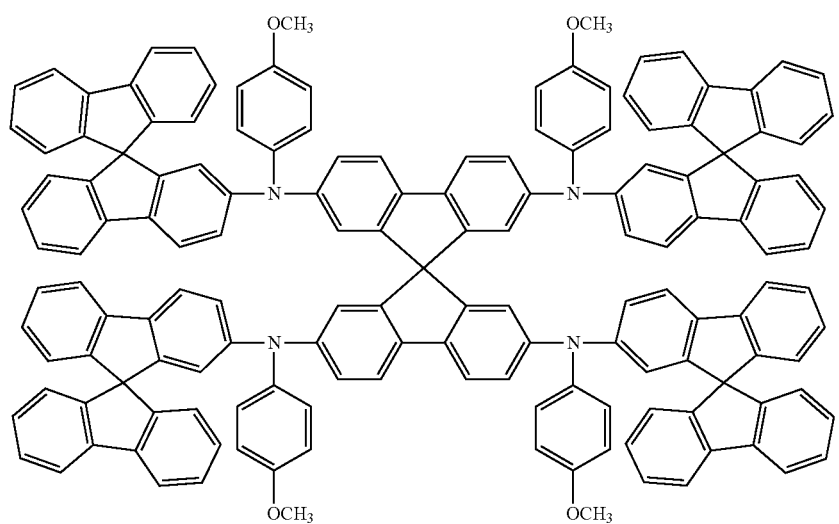
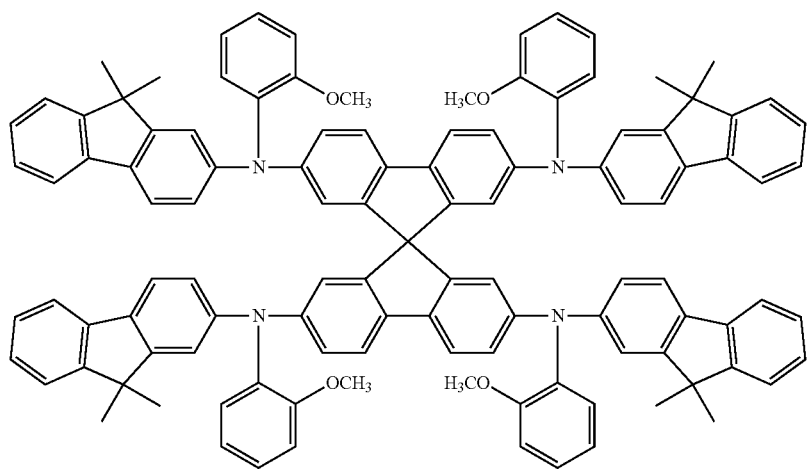

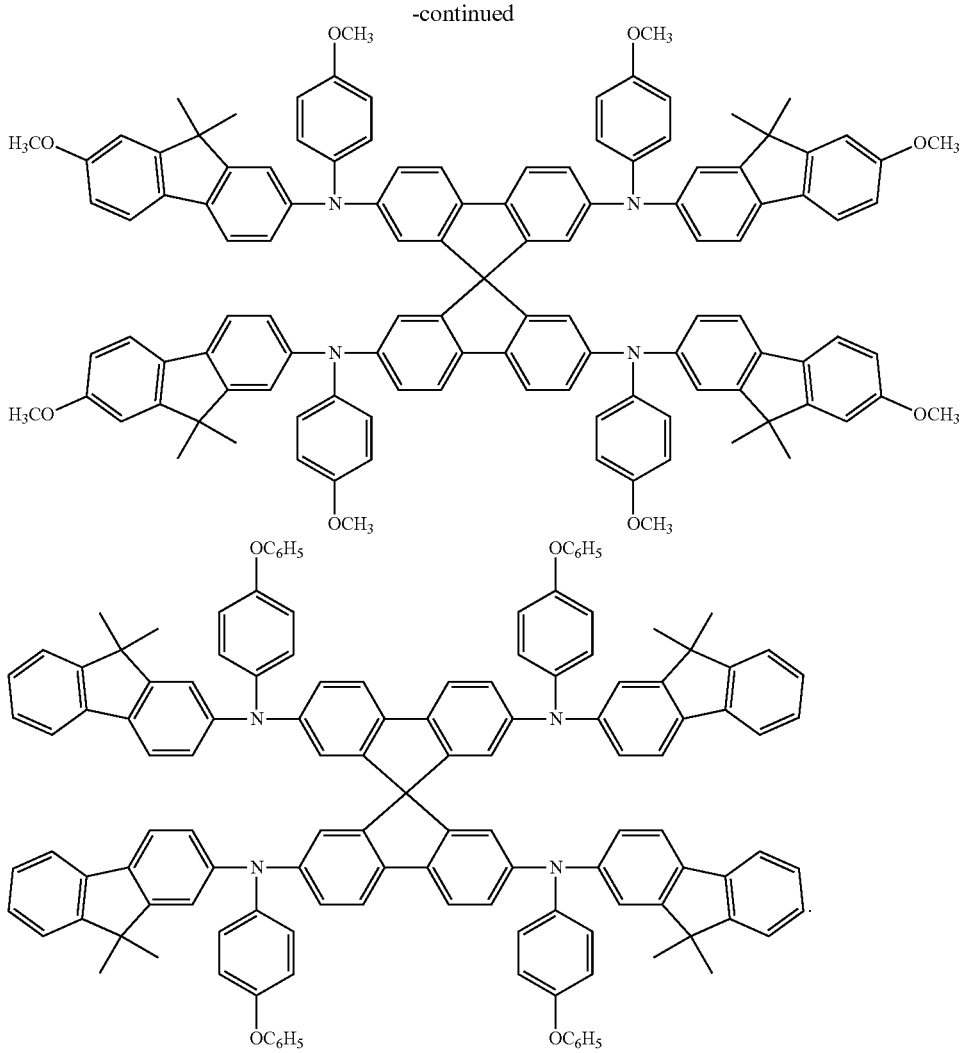

In Chemical Formula 2 or 3 of the present invention, when $R_{11}$ and $R_{12}$ are independently of each other (C1-C10) alkyl or (C6-C12)aryl, photoelectric transformation efficiency is higher, and $R_{11}$ and $R_{12}$ may be preferably methyl, ethyl, propyl, isopropyl, n-butyl, isobutyl, tert-butyl, or phenyl.

The hole transport compound represented by Chemical Formula 1 of the present invention may be prepared by the following reaction formula, as an example:

[Reaction Formula 1]

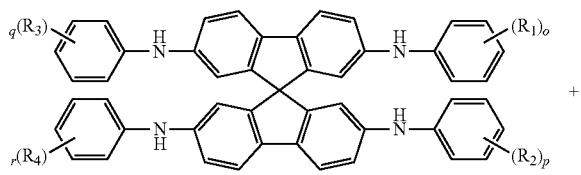

+

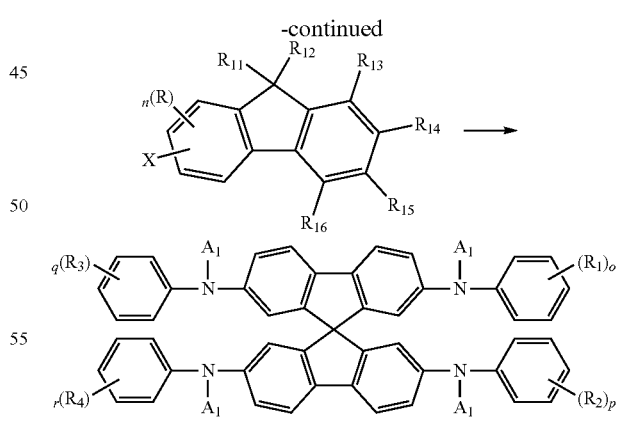

wherein $A_1$, $R_1$ to $R_4$, R, $R_{11}$ to $R_{16}$, n, o, p, q, and r are as defined in Chemical Formula 1, and X is a halogen.

Reaction Formula 1 corresponds to the case in which $A_1$ to $A_4$ are identical, and when $A_1$ to $A_4$ are different from each other, the compound of Chemical Formula 1 may certainly be prepared by a synthesis method which may be recognized by a person skilled in the art.

The terms, "alkyl", "alkoxy" and other substituents including the "alkyl" part, described herein, include all forms of straight chain and branched chain.

In addition, "aryl" described in the present invention refers to an organic radical derived from aromatic hydrocarbon by removal of one hydrogen, including a single- or fused ring system containing appropriately 4 to 7, preferably 5 or 6 ring atoms in each ring, and even a form in which a plurality of aryls are linked by a single bond. A specific example thereof includes phenyl, naphthyl, biphenyl, anthryl, indenyl, fluorenyl, spirobifluorene, or the like, but not limited thereto.

"Heteroaryl" described in the present invention refers to an aryl group containing 1 to 4 heteroatoms selected from the group consisting of B, N, O, S, P(=O), Si, and P as an aromatic ring backbone atom, and carbons as remaining aromatic ring backbone atoms, and is a 5- or 6-membered monocyclic heteroaryl and a polycyclic heteroaryl fused with one or more benzene rings, which may be partially saturated. In addition, the heteroaryl in the present invention also includes a form in which one or more heteroaryls are linked by a single bond.

"Arylalkyl" described alone or as a portion of another group in the present invention refers to a functional group in which one or more hydrogens of an alkyl group are substituted with aryl, and as an example, may be benzyl or the like.

A spirocycle fused with an aromatic ring described in the present invention may be a spirocycle fused with a $C_6$-$C_{12}$ aromatic cyclic compound, and as an example, spirofluorene, and specifically, the spirocycle of the present invention which is fused with an aromatic ring formed by $R_{11}$ and $R_{12}$ linked to each other may be

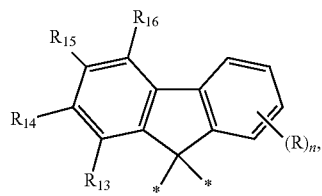

and preferably

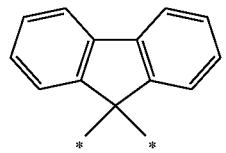

The spirobifluorene compound according to an exemplary embodiment of the present invention may interact with a hole transport layer and a light absorption layer including the compound of a perovskite structure to be used as a buffer layer, but preferably may be used as the hole transport material of the perovskite solar cell.

The perovskite solar cell according to an exemplary embodiment of the present invention may include a first electrode, an electron transport layer formed on the first electrode, a light absorption layer including a compound having a perovskite structure formed on the electron transport layer, a hole transport layer including a spirobifluorene compound represented by Chemical Formula 1, formed on the light absorption layer, and a second electrode formed on the hole transport layer.

The parts corresponding to each component of the perovskite solar cell according to an exemplary embodiment of the present invention include the descriptions of International Patent Application No. PCT-KR2014-012727, except the hole transport layer necessarily including the spirobisfluorene compound represented by Chemical Formula 1.

Specifically, a first electrode according to an exemplary embodiment of the present invention is all possible as long as it is a conductive electrode forming an ohmic junction with an electron transport layer, and a second electrode is all possible as long as it is a conductive electrode forming an ohmic junction with a hole transport layer.

In addition, the first and second electrodes may be any material commonly used as an electrode material of a front electrode or a back electrode in a solar cell. As a non-limiting example, when the first and second electrodes are the electrode material of a back electrode, the first and second electrodes may be one or more materials selected from the group consisting of gold, silver, platinum, palladium, copper, aluminum, carbon, cobalt sulfide, copper sulfide, nickel oxide, and a composite thereof. As a non-limiting example, when the first and second electrodes are transparent electrodes, the first and second electrodes may be inorganic-based conductive electrodes such as a fluorine doped tin oxide (FTO), an indium doped tin oxide (ITO), ZnO, CNT (carbon nanotube) or graphene, or organic-based conductive electrodes such as PEDOT:PSS. In the case of providing a transparent solar cell, it is preferred that the first and second electrodes are transparent electrodes, and when providing a flexible solar cell or a transparent solar cell, it is preferred that the first and second electrodes are organic-based conductive electrodes.

The first electrode may be formed on a rigid substrate or flexible substrate using deposition or coating. Deposition may be physical vapor deposition or chemical vapor deposition, and also may be carried out by thermal evaporation. Coating may be carried out by coating a solution or dispersion of the electrode material on the substrate and then drying, or subjecting a dried film to heat treatment selectively. However, of course, the first and second electrodes may be formed using a method used for forming a front electrode or a back electrode in a common solar cell.

The electron transport layer formed on the upper portion of the first electrode of the present invention may be an electron conductive organic layer or inorganic layer. The electron conductive organic material may be an organic material used as an n-type semiconductor, in a general organic solar cell. As a specific and non-limiting example, the electron conductive organic material may include fullerene (C60, C70, C74, C76, C78, C82, C95), fullerene-derivatives including PCBM ([6,6]-phenyl-$C_{61}$-butyric acid methyl ester) and C71-PCBM, C84-PCBM, $PC_{70}BM$ ([6,6]-phenyl $C_{70}$-butyric acid methyl ester), PBI (polybenzimidazole), PTCBI (3,4,9,10-perylenetetracarboxylic bisbenzimidazole), F4-TCNQ (tetrafluorotetracyanoquinodimethane), or a mixture thereof. The electron conductive inorganic material may be an electron conductive metal oxide used for electron transfer, in a general quantum dot based solar cell or dye-sensitized solar cell. As a specific example, the electron conductive metal oxide may be an n-type metal oxide semiconductor. A non-limiting example of the n-type metal oxide semiconductor may include one or two or more materials selected from the group consisting of Ti oxides, Zn oxides, In oxides, Sn oxides, W oxides, Nb oxides, Mo oxides, Mg oxides, Ba oxides, Zr oxides, Sr oxides, Yr oxides, La oxides, V oxides, Al oxides, Y oxides, Sc oxides, Sm oxides, Ga oxides, In oxides and SrTi oxides, and also a mixture or composite thereof.

The light absorption layer formed on the electron transport layer according to an exemplary embodiment of the perovskite solar cell of the present invention includes a compound having a perovskite structure, and as the compound having a perovskite structure, all compounds included in a range recognized by a person skilled in the art to which the present invention pertains are possible.

As an example, the compound refers to a compound containing a monovalent organic cation, a divalent metal cation, and a halogen anion and having a perovskite structure.

As a specific example, the compound having a perovskite structure of the present invention may be one or two or more materials selected from the perovskite compounds satisfying the following Chemical Formulae 11 and 12:

$$AMX_3 \quad \text{[Chemical Formula 11]}$$

wherein A is a monovalent organic ammonium ion or $Cs^+$, M is a divalent metal ion, and X is a halogen ion, $$A_2MX_4 \quad \text{[Chemical Formula 12]}$$

wherein A is a monovalent organic ammonium ion or $Cs^+$, M is a divalent metal ion, and X is a halogen ion.

Here, M is positioned at a center of a unit cell in the perovskite structure, X is positioned at a center of each face of the unit cell, and forms an octahedron structure having M in the center, and A is positioned at each corner of the unit cell.

Specifically, the light absorption layer may be independently of each other one or two or more selected from the compounds satisfying Chemical Formulae 13 to 16:

$$(R_1\text{—}NH_{3+})MX_3 \quad \text{[Chemical Formula 13]}$$

wherein $R_1$ is C1-C24 alkyl, C3-C20 cycloalkyl, or C6-C20 aryl, M is one or two or more metal ions selected from $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, and $Yb_{2+}$, and X is one or two or more halogen ions selected from $Cl^-$, $Br^-$, and $I^-$.

$$(R_1\text{—}NH_{3+})_2MX_4 \quad \text{[Chemical Formula 14]}$$

wherein $R_1$ is C1-C24 alkyl, C3-C20 cycloalkyl, or C6-C20 aryl, M is one or two or more metal ions selected from $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, and $Yb^{2+}$, and X is one or two or more halogen ions selected from $Cl^-$, $Br^-$, and $I^-$.

$$(R_2\text{—}C_3H_3N_2^+\text{—}R_3)MX_3 \quad \text{[Chemical Formula 15]}$$

wherein $R_2$ is C1-C24 alkyl, C3-C20 cycloalkyl, or C6-C20 aryl, $R_3$ is hydrogen or C1-C24 alkyl, M is one or two or more metal ions selected from $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, and $Yb^{2+}$, and X is one or two or more halogen ions selected from $Cl^-$, $Br^-$, and $I^-$.

$$(R_2\text{—}C_3H_3N_2^+\text{—}R_3)_2MX_4 \quad \text{[Chemical Formula 16]}$$

wherein $R_2$ is C1-C24 alkyl, C3-C20 cycloalkyl, or C6-C20 aryl, $R_3$ is hydrogen or C1-C24 alkyl, M is one or two or more metal ions selected from $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, and $Yb^{2+}$, and X is one or two or more halogen ions selected from $Cl^-$, $Br^-$, or $I^-$.

As an example, the compound of perovskite structure may be $AMX^a_xX^b_y$ or $A_2MX^a_xX^b_y$ (x is a real number of 0<x<3, y is a real number of 0<y<3, x+y=3, and $X^a$ and $X^b$ are halogens different from each other).

As an example, in Chemical Formula 13 or 14, $R_1$ may be C1-C24 alkyl, preferably C1-C7 alkyl, more preferably methyl. Specifically, as an example, the compound having a perovskite structure may be one or two or more selected from $CH_3NH_3PbI_xCl_y$ (x is a real number of 0≤x≤3, y is a real number of 0≤y≤3, and x+y=3), $CH_3NH_3PbI_xBr_y$ (x is a real number of 0≤x≤3, y is a real number of 0≤y≤3, and x+y=3), $CH_3NH_3PbCl_xBr_y$ (x is a real number of 0 x≤3, y is a real number of 0≤y≤3, and x+y=3), and $CH_3NH_3PbI_xF_y$ (x is a real number of 0≤x≤3, y is a real number of 0≤y≤3, and x+y=3), and also, one or two or more selected from $(CH_3NH_3)_2PbI_xCl_y$ (x is a real number of 0≤x≤4, y is a real number of 0≤y≤4, and x+y=4), $CH_3NH_3PbI_xBr_y$ (x is a real number of 0≤x≤4, y is a real number of 0≤y≤4, and x+y=4), $CH_3NH_3PbCl_xBr_y$ (x is a real number of 0≤x≤4, y is a real number of 0≤y≤4, and x+y=4), and $CH_3NH_3PbI_xF_y$ (x is a real number of 0≤x≤4, y is a real number of 0≤y≤4, and x+y=4)

As an example, in Chemical Formula 15 or 16, $R_2$ may be C1-C24 alkyl, $R_3$ may be hydrogen or C1-C24 alkyl, preferably $R_2$ is C1-C7 alkyl, and $R_3$ may be hydrogen or C1-C7 alkyl, and more specifically $R_2$ may be methyl, and $R_3$ may be hydrogen.

Preferably, the compound having a perovskite structure according to an exemplary embodiment of the present invention may be represented by the following Chemical Formula 17:

[Chemical Formula 17]

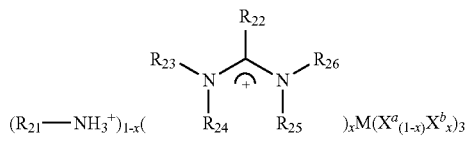

wherein $R_{21}$ is a C1-C24 alkyl group, a C3-C20 cycloalkyl group, or C6-C20 aryl group, $R_{22}$ to $R_{26}$ are independently of one another hydrogen, a C1-C24 alkyl group, a C3-C20 cycloalkyl group, or a C6-C20 aryl group, M is a divalent metal ion, $X^a$ is an iodine ion, $X^b$ is a bromine ion, and x is a real number of 0.1≤x≤0.3.

Preferably, the light absorption layer according to an exemplary embodiment of the present invention may be a compound having a perovskite structure containing lead.

The hole transport layer of the perovskite solar cell according to an exemplary embodiment of the present invention necessarily includes the spirobisfluorene compound represented by Chemical Formula 1.

Specifically, the hole transport layer of the present invention is a hole transport material which necessarily includes the spirobisfluorene compound represented by Chemical Formula 1 of the present invention, may include the spirobisfluorene compound alone, and may further include an organic hole transport material, an inorganic hole transport material, or a mixture thereof, except the spirobisfluorene compound represented by Chemical Formula 1. When the hole transport material is the inorganic hole transport material, the inorganic hole transport material may be an oxide semiconductor, a sulfide semiconductor, a halide semiconductor or a mixture thereof, which has hole conductivity, that is, which is a p-type semiconductor. An example of the oxide semiconductor may include NiO, CuO, $CuAlO_2$, $CuGaO_2$ and the like, an example of the sulfide semiconductor may include PbS, and an example of the halide semiconductor may include $PbI_2$ and the like, but the present invention is not limited thereto.

When the hole transport material is the organic hole transport material, a monomolecular or high molecular organic hole transport material (hole conductive organic material) may be included. The organic hole transport material may be any material used in a common inorganic semiconductor-based solar cell using an inorganic semiconductor quantum dot as dye. A non-limiting example of a monomolecular to low molecular organic hole transport material may include one or two or more materials selected from the group consisting of pentacene, coumarin 6,3-(2-benzothiazolyl)-7-(diethylamino)coumarin), ZnPC (zinc phthalocyanine), CuPC (copper phthalocyanine), TiOPC (titanium oxide phthalocyanine), Spiro-MeOTAD (2,2',7,7'-tetrakis(N,N-p-dimethoxyphenylamino)-9,9'-spirobifluorene), F16CuPC (copper(II) 1,2,3,4,8,9,10,11,15,16,17,18,22,23,24,25-hexadecafluoro-29H,31H-phthalocyanine), SubPc (boron subphthalocyanine chloride), and N3 (cis-di(thiocyanato)-bis(2,2'-bipyridyl-4,4'-dicarboxylic acid)-ruthenium(II)), but not limited thereto. The present invention is not limited to the materials.

The hole transport layer according to an exemplary embodiment of the present invention may be formed of a hole transport material including the spirobisfluorene compound represented by Chemical Formula 1 by a solution process. The solution process performed by an exemplary embodiment of the present invention may be, as an example, screen printing, spin coating, bar coating, gravure coating, blade coating, roll coating, or the like, but not limited thereto.

Hereinafter, the present invention will be described in detail, by the specific examples of the present invention, however, the examples does not limit the scope of the claims of the present invention.

[Example 1] Preparation of Compound 1

Preparation of Compound 1-1

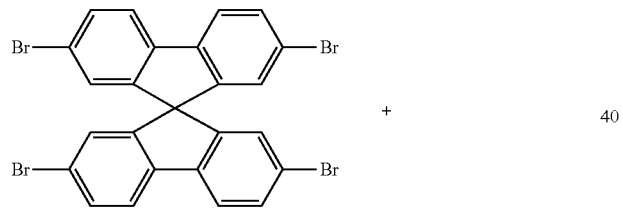

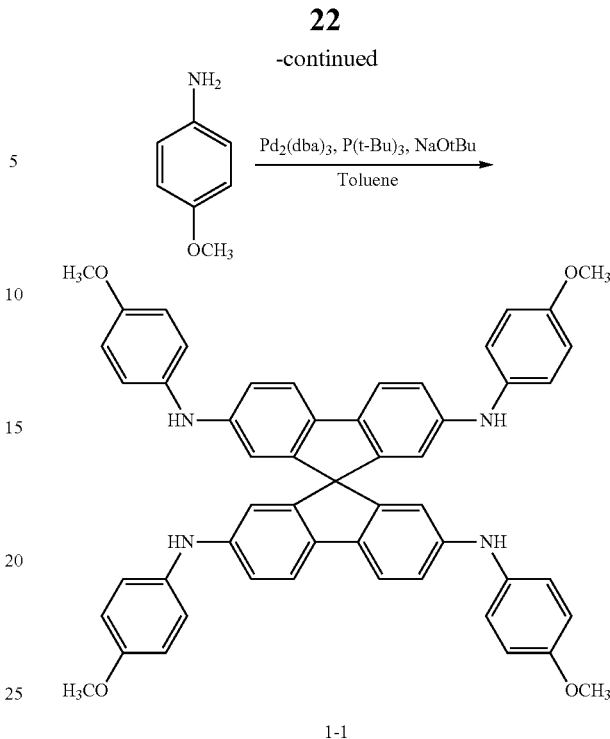

1-1

Tris(dibenzylideneacetone)dipalladium(0) (1.30 g, 1.4240 mmol), tri-tert-butylphosphine (0.58 g, 2.8480 mmol), and toluene (20 mL) were added to a 250 mL two-necked flask, and stirred for 10 minutes under a nitrogen atmosphere. 2,2',7,7'-Tetrabromo-9,9'-spirobi[9H-fluorene] (3 g, 4.7468 mmol) and toluene (20 mL) were added thereto and stirred for 10 minutes, sodium tert-butoxide (3.65 g, 37.9744 mmol), p-anisidine (5.85 g, 47.468 mmol), and toluene (15 mL) were added thereto and reacted at 130° C. for 30 hours. After completing the reaction, the reactant was extracted using ethyl acetate and NaCl water, and moisture was removed with $MgSO_4$. Purification was performed with column chromatography (ethyl acetate/hexane=40%), and recrystallization was performed using methylene chloride and hexane, thereby obtaining Compound 1-1 (2.16 g, 58%) in a powder form.

Preparation of Compound 1

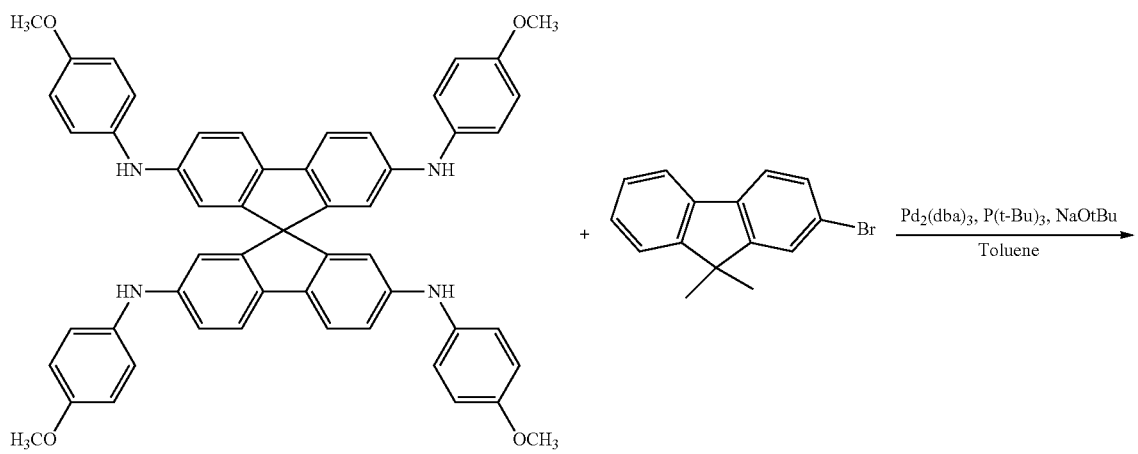

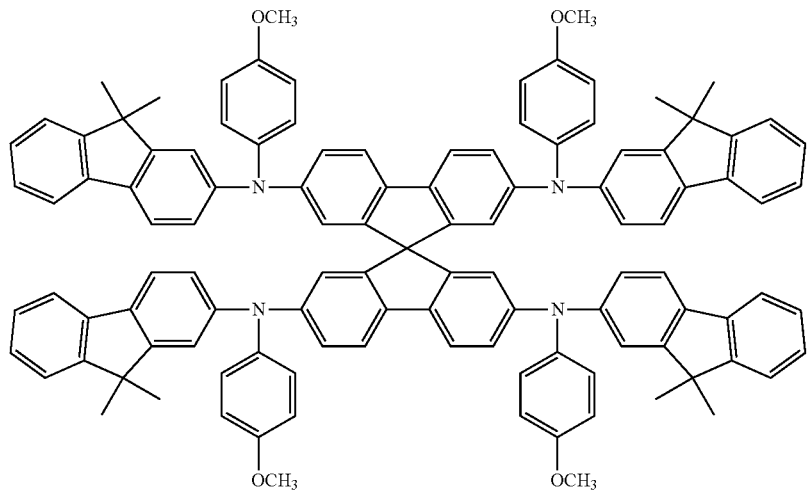

1

Tris(dibenzylideneacetone)dipalladium (0) (0.28 g, 0.3 mmol), tri-tert-butylphosphine (0.12 g, 0.6 mmol), and toluene (10 mL) were added to a 250 mL two-necked flask, and stirred for 10 minutes under a nitrogen atmosphere. 2-bromo-9,9-dimethylfluorene (0.8 g, 1 mmol) and toluene (10 mL) were added thereto and stirred for 10 minutes, sodium tert-butoxide (0.86 g, 9 mmol), Compound 1-1 (0.80 g, 1 mmol), and toluene (15 mL) were added thereto and reacted at 130° C. for 30 hours. After completing the reaction, the reactant was extracted using ethyl acetate and NaCl water, and moisture was removed with $MgSO_4$. Purification was performed with column chromatography (ethyl acetate/hexane=20%), and reprecipitation was performed using methylene chloride and hexane, thereby obtaining Compound 1 (0.8 g, 51%) in a powder form.

$^1$H-NMR (Acetone, 400 MHz) δ=7.65 (d, 4H), 7.60 (d, 4H), 7.43 (d, 8H), 7.21 (m, 8H), 7.19 (s, 4H), 7.07 (d, 8H), 6.91 (d, 8H), 6.86 (d, 4H), 6.81 (d, 4H), 6.67 (s, 4H), 3.80 (s, 12H), 1.33 (s, 24H).

[Example 2] Preparation of Compound 2

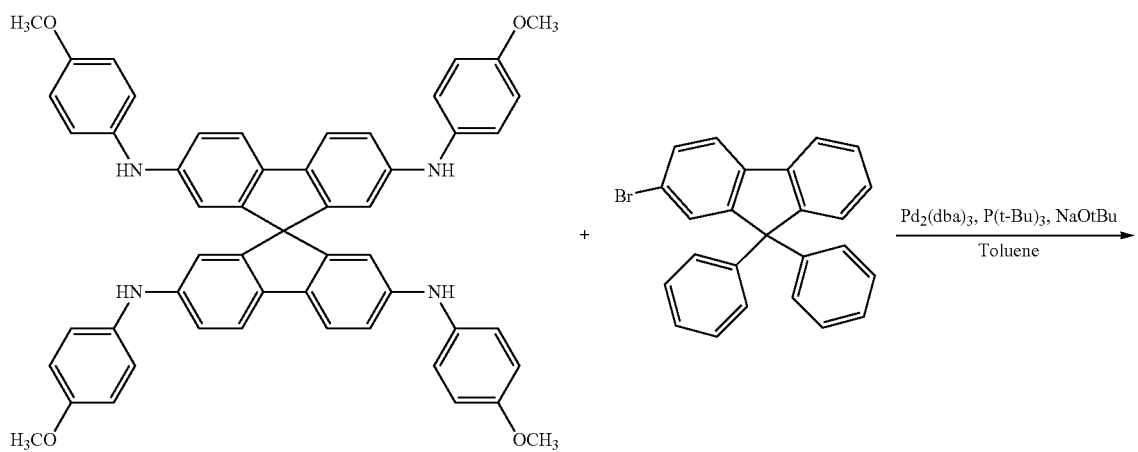

-continued

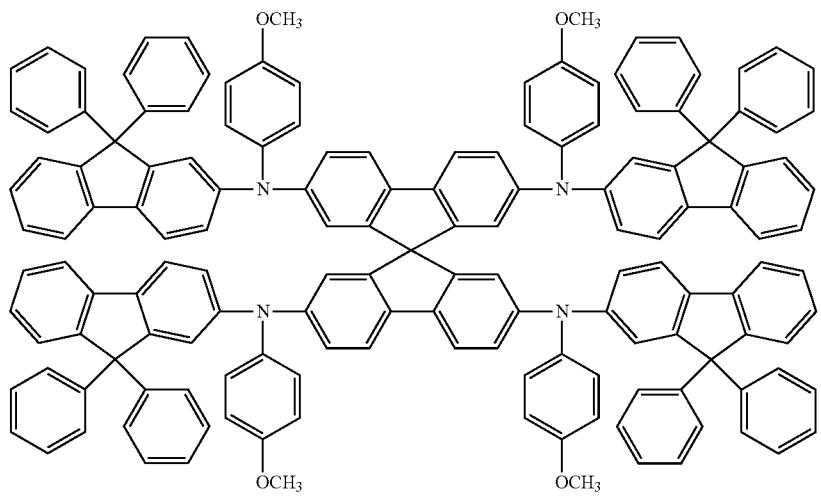

2

Tris(dibenzylideneacetone)dipalladium(0) (0.21 g, 0.2247 mmol), tri-tert-butylphosphine (0.09 g, 0.4495 mmol), and toluene (10 mL) were added to a 250 mL two-necked flask, and stirred for 10 minutes under a nitrogen atmosphere. 2-bromo-9,9-diphenylfluorene (1.49 g, 3.7455 mmol) and toluene (10 mL) were added thereto and stirred for 10 minutes, sodium tert-butoxide (0.65 g, 6.7419 mmol), Compound 1-1 (0.60 g, 0.7491 mmol), and toluene (15 mL) were added thereto and reacted at 130° C. for 30 hours. After completing the reaction, the reactant was extracted using ethyl acetate and NaCl water, and moisture was removed with MgSO$_4$. Purification was performed with column chromatography (ethyl acetate/hexane=20%), and reprecipitation was performed using methylene chloride and hexane, thereby obtaining Compound 2 (0.79 g, 51%) in a powder form.

$^1$H-NMR (Acetone, 400 MHz) δ=7.73 (d, 4H), 7.65 (d, 4H), 7.46 (d, 4H), 7.39 (d, 4H), 7.32 (t, 4H), 7.16 (m, 28H), 7.08 (d, 16H), 7.04 (s, 4H), 6.87 (t, 16H), 6.76 (d, 8H), 6.52 (s, 4H), 3.72 (s, 12H).

[Example 3] Preparation of Compound 3

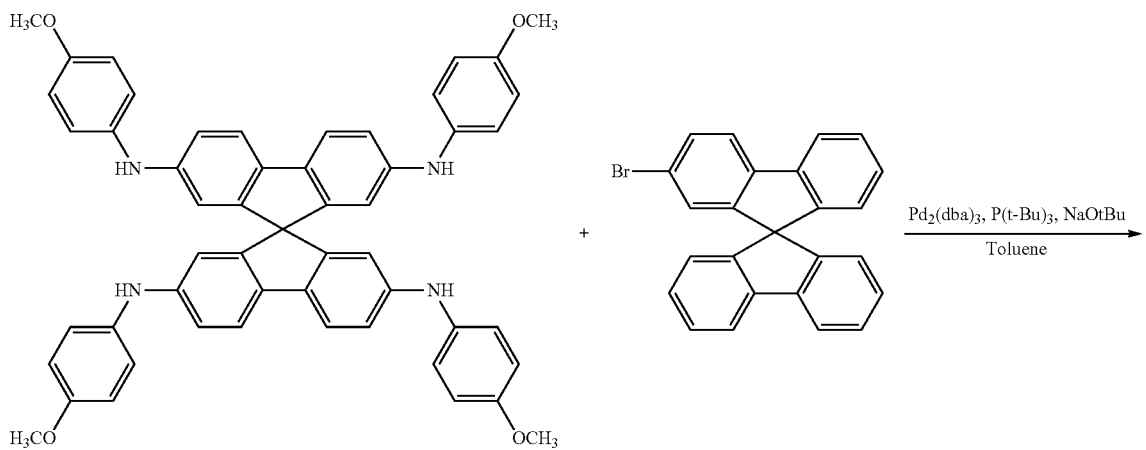

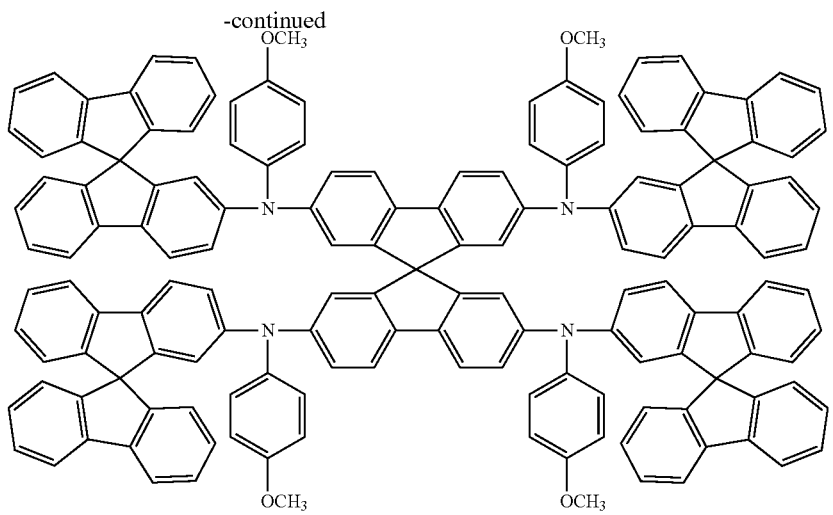

3

Tris(dibenzylideneacetone)dipalladium(0) (0.46 g, 0.4994 mmol), tri-tert-butylphosphine (0.20 g, 0.9988 mmol), and toluene (20 mL) were added to a 250 mL two-necked flask, and stirred for 10 minutes under a nitrogen atmosphere. 2-bromo-9,9-spirobi[9H-fluorene] (2.47 g, 6.2425 mmol) and toluene (20 mL) were added thereto and stirred for 10 minutes, sodium tert-butoxide (1.08 g, 11.2365 mmol), Compound 1-1 (1 g, 1.2485 mmol), and toluene (30 mL) were added thereto and reacted at 130° C. for 30 hours. After completing the reaction, the reactant was extracted using ethyl acetate and NaCl water, and moisture was removed with MgSO$_4$. Purification was performed with column chromatography (ethyl acetate/hexane=20%), and reprecipitation was performed using methylene chloride and hexane, thereby obtaining Compound 3 (2.02 g, 79%) in a powder form.

$^1$H-NMR (Acetone, 400 MHz) δ=7.79 (t, 12H), 7.70 (d, 4H), 7.38 (d, 4H), 7.29 (t, 12H), 7.09 (t, 8H), 7.02 (t, 4H), 6.87 (d, 4H), 6.75 (d, 4H), 6.68 (d, 16H), 6.55 (t, 12H), 6.36 (s, 4H), 6.28 (s, 4H), 3.60 (s, 12H).

[Example 4] Preparation of Compound 4

Preparation of Compound 4-1

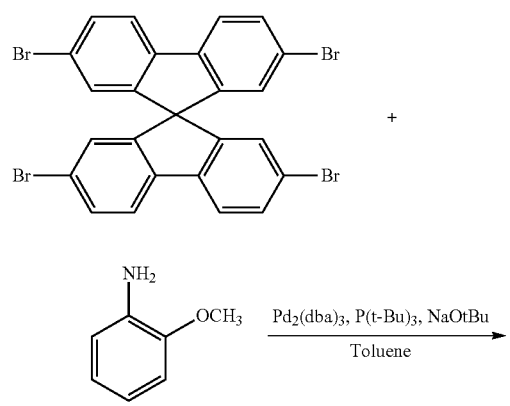

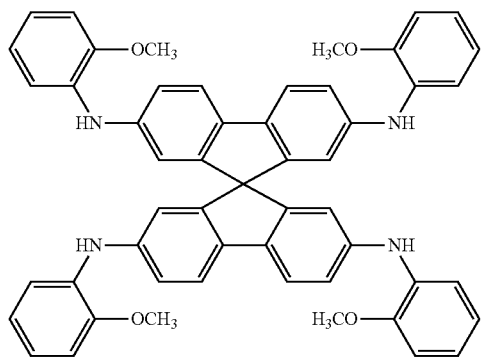

4-1

Tris(dibenzylideneacetone)dipalladium(0) (0.87 g, 0.9494 mmol), tri-tert-butylphosphine (0.51 g, 1.8988 mmol), and toluene (20 mL) were added to a 250 mL two-necked flask, and stirred for 10 minutes under a nitrogen atmosphere. 2,2',7,7'-Tetrabromo-9,9'-spirobi[9H-fluorene] (2 g, 3.1646 mmol) and toluene (20 mL) were added thereto and stirred for 10 minutes, sodium tert-butoxide (3.04 g, 31.64 mmol), o-anisidine (3.90 g, 31.6456 mmol), and toluene (30 mL) were added thereto and reacted at 130° C. for 30 hours. After completing the reaction, the reactant was extracted using ethyl acetate and NaCl water, and moisture was removed with MgSO$_4$. Purification was performed with column chromatography (ethyl acetate/hexane=40%), and reprecipitation was performed using methylene chloride and hexane, thereby obtaining Compound 4-1 (2.06 g, 81%) in a powder form.

Preparation of Compound 4

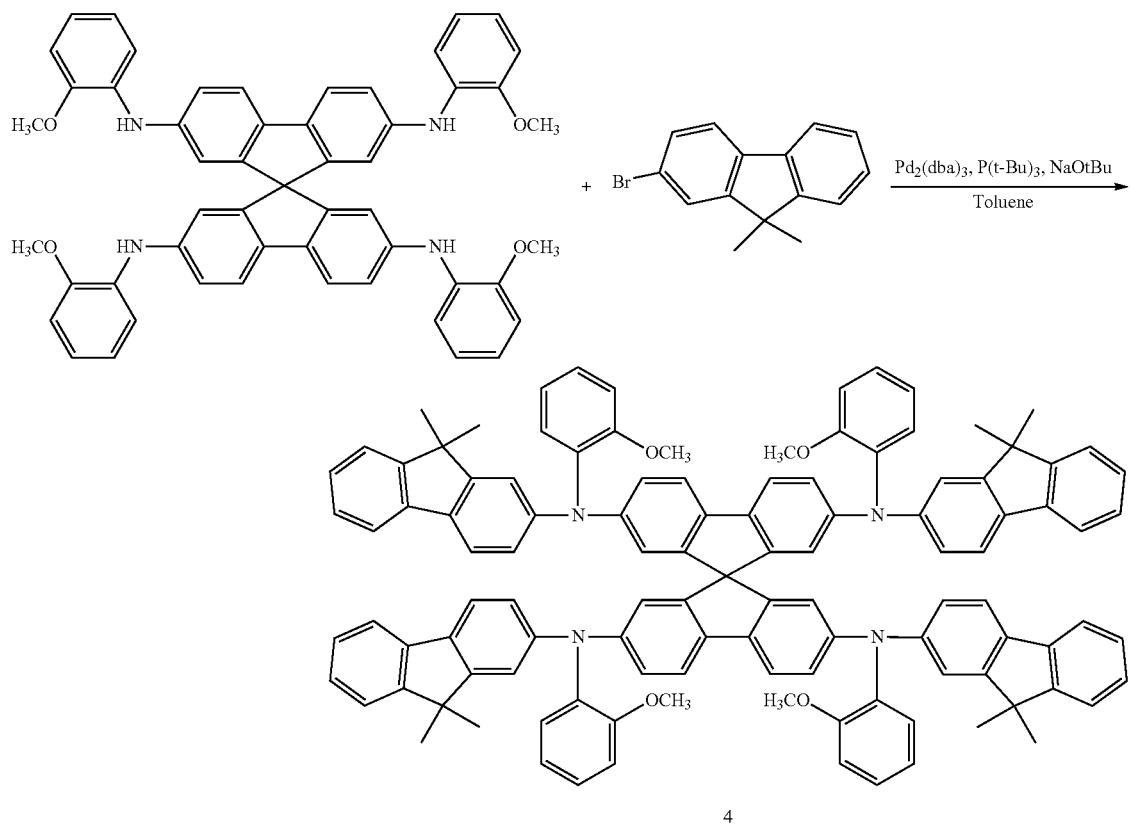

4

Tris(dibenzylideneacetone)dipalladium (0) (0.51 g, 0.3 mmol), tri-tert-butylphosphine (0.22 g, 1.1237 mmol), and toluene (20 mL) were added to a 250 mL two-necked flask, and stirred for 10 minutes under a nitrogen atmosphere. 2-bromo-9,9-dimethylfluorene (2.56 g, 9.3640 mmol) and toluene (20 mL) were added thereto and stirred for 10 minutes, sodium tert-butoxide (1.62 g, 16.8552 mmol), Compound 4-1 (1.5 g, 1.8728 mmol), and toluene (30 mL) were added thereto and reacted at 130° C. for 30 hours. After completing the reaction, the reactant was extracted using ethyl acetate and NaCl water, and moisture was removed with MgSO$_4$. Purification was performed with column chromatography (ethyl acetate/hexane=20%), and reprecipitation was performed using methylene chloride and hexane, thereby obtaining Compound 4 (1.72 g, 59%) in a powder form.

$^1$H-NMR (Acetone, 400 MHz) δ=7.63 (d, 4H), 7.56 (d, 4H), 7.39 (m, 8H), 7.16 (m, 16H), 7.13 (s, 4H), 7.06 (d, 4H), 6.97 (t, 4H), 6.80 (d, 4H), 6.75 (d, 4H), 6.62 (s, 4H), 3.56 (s, 12H), 1.32 (s, 24H).

[Example 5] Preparation of Compound 5

Preparation of Compound 5-1

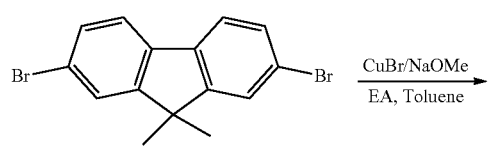

-continued

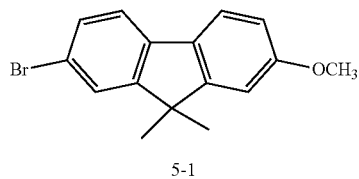

5-1

2,7-dibromo-9,9-dimethylfluorene (4.06 g, 11.5318 mmol), copper bromide (0.83 g, 5.7659 mmol), ethyl acetate (5 mL), and toluene (5 mL) were added to a 500 mL two-necked flask, and stirred for 10 minutes under a nitrogen atmosphere. Thereafter, sodium methoxide solution (200 mL) was added thereto, and reacted at 80° C. for 3 hours. After completing the reaction, the reactant was extracted using methylene chloride and NaCl water, and moisture was removed with MgSO$_4$. Purification was performed with column chromatography (methylene chloride/hexane=25%), thereby obtaining Compound 5-1 (1.4 g, 80%) in a powder form.

Preparation of Compound 5

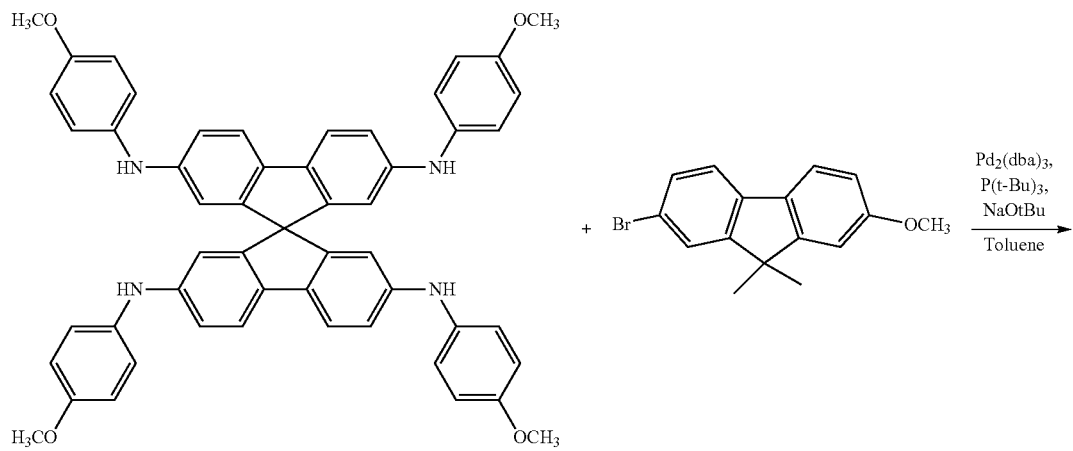

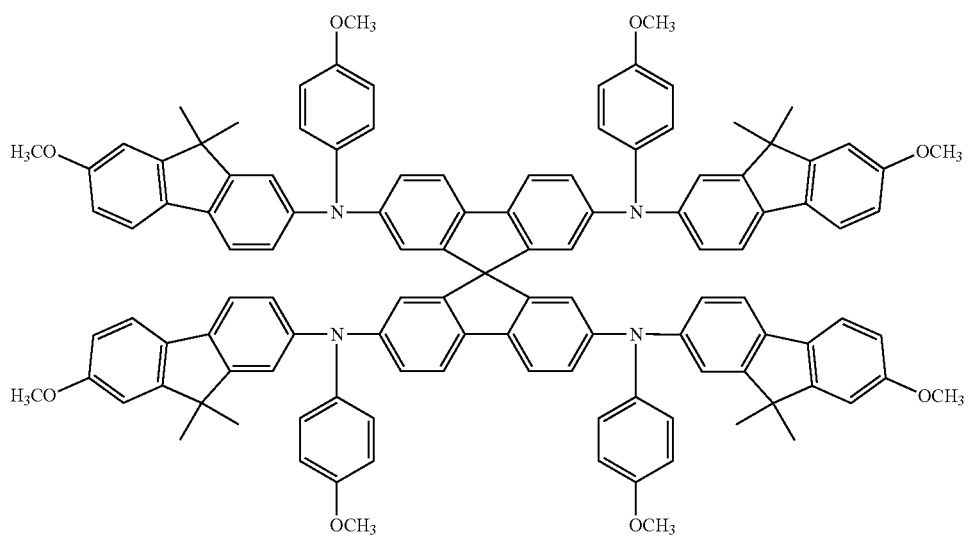

Tris(dibenzylideneacetone)dipalladium(0) (0.17 g, 0.1882 mmol), tri-tert-butylphosphine (0.08 g, 0.3763 mmol), and toluene (10 mL) were added to a 250 mL two-necked flask, and stirred for 10 minutes under a nitrogen atmosphere. 2-bromo-7-methoxy-9,9-dimethylfluorene (0.95 g, 3.136 mmol) and toluene (10 mL) were added thereto and stirred for 10 minutes, sodium tert-butoxide (0.54 g, 5.6448 mmol), Compound 1-1 (0.5 g, 0.6272 mmol), and toluene (15 mL) were added thereto and reacted at 130° C. for 30 hours. After completing the reaction, the reactant was extracted using ethyl acetate and NaCl water, and moisture was removed with $MgSO_4$. Purification was performed with column chromatography (ethyl acetate/hexane=20%), and reprecipitation was performed using methylene chloride and hexane, thereby obtaining Compound 5 (0.52 g, 49%) in a powder form.

$^1$H-NMR (Acetone, 400 MHz) δ=7.57 (d, 4H), 7.51 (d, 4H), 7.42 (d, 4H), 7.17 (s, 4H), 7.06 (d, 12H), 6.90 (d, 8H), 6.84 (t, 8H), 6.78 (d, 4H), 6.63 (s, 4H), 3.84 (s, 12H), 3.81 (s, 12H), 1.33 (s, 24H).

[Example 6] Preparation of Compound 6

Preparation of Compound 6-1

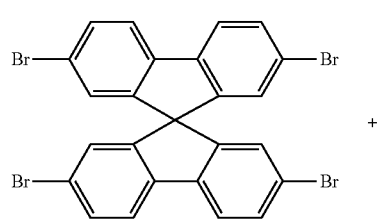

+

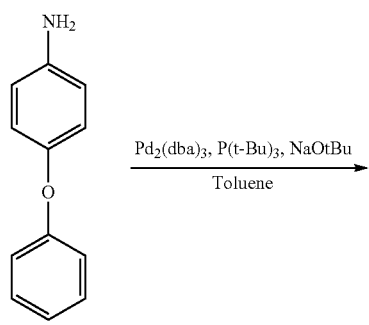

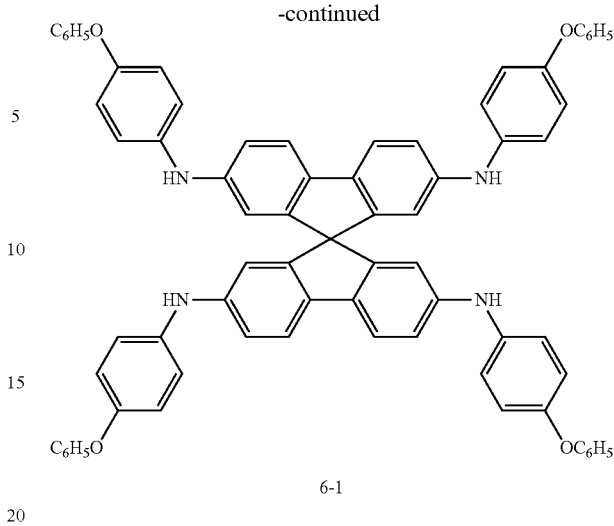

Tris(dibenzylideneacetone)dipalladium(0) (0.65 g, 0.7120 mmol), tri-tert-butylphosphine (0.29 g, 1.4240 mmol), and toluene (10 mL) were added to a 250 mL two-necked flask, and stirred for 10 minutes under a nitrogen atmosphere. 2,2',7,7'-Tetrabromo-9,9'-spirobi[9H-fluorene] (1.5 g, 2.6732 mmol) and toluene (10 mL) were added thereto and stirred for 10 minutes, sodium tert-butoxide (1.82 g, 18.9872 mmol), 4-phenoxyaniline (4.39 g, 23,734 mmol), and toluene (15 mL) were added thereto and reacted at 130° C. for 30 hours. After completing the reaction, the reactant was extracted using ethyl acetate and NaCl water, and moisture was removed with MgSO$_4$. The reaction mixture was purified by column chromatography (ethyl acetate/hexane=40%), and reprecipitation was performed using methylene chloride and hexane, thereby obtaining a product (1.45 g, 58%) in a powder form.

Preparation of Compound 6

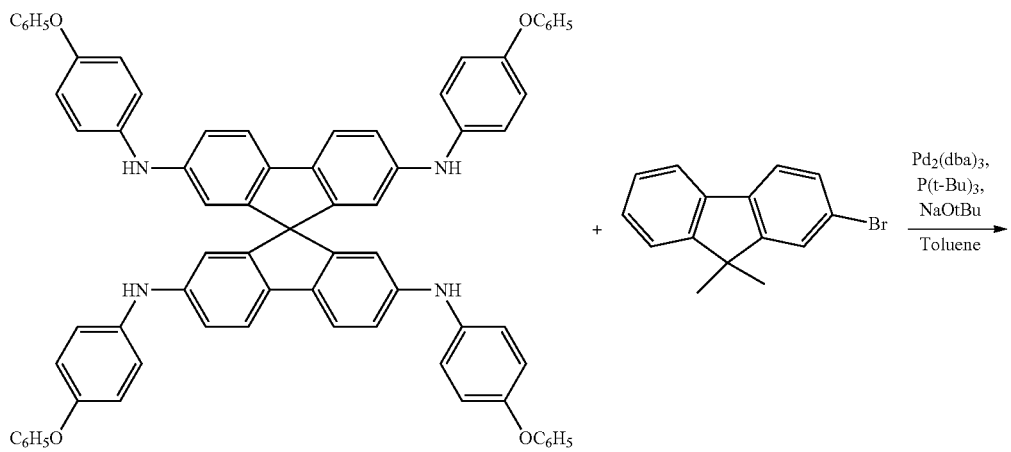

-continued

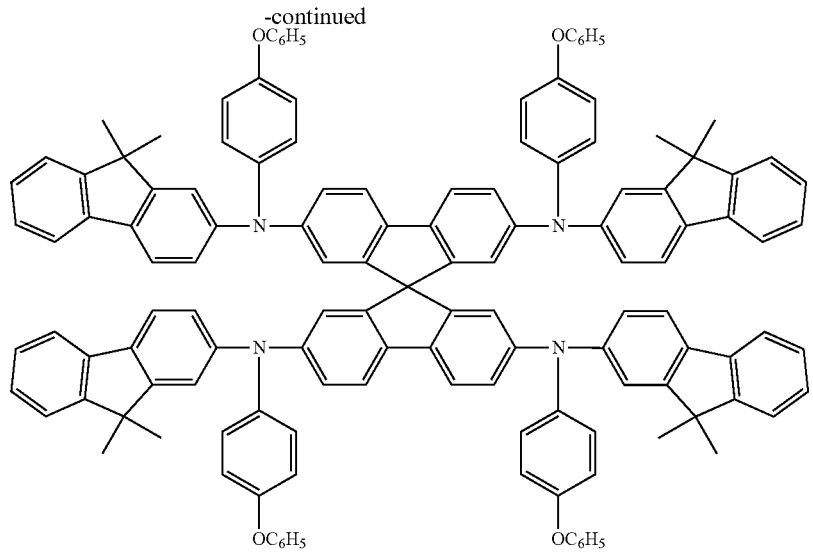

6

Tris(dibenzylideneacetone)dipalladium(0) (0.28 g, 0.3 mmol), tri-tert-butylphosphine (0.12 g, 0.6 mmol), and toluene (10 mL) were added to a 250 mL two-necked flask, and stirred for 10 minutes under a nitrogen atmosphere. 2-bromo-9,9-dimethylfluorene (0.8 g, 1 mmol) and toluene (10 mL) were added thereto and stirred for 10 minutes, sodium tert-butoxide (0.86 g, 9 mmol), Compound 6-1 (1.05 g, 1 mmol), and toluene (15 mL) were added thereto and reacted at 130° C. for 30 hours. After completing the reaction, the reactant was extracted using ethyl acetate and NaCl water, and moisture was removed with $MgSO_4$. The remaining solution was distilled under reduced pressure and purified by column chromatography (ethyl acetate/hexane=20%), and reprecipitation was performed using methylene chloride and hexane, thereby obtaining compound 6 (0.9 g, 48%) in a powder form.

$^1$H-NMR (Acetone, 400 MHz) δ=7.64 (d, 4H), 7.60 (d, 4H), 7.42 (d, 8H), 7.22 (m, 8H), 7.18 (s, 4H), 7.07 (m, 16H), 7.02 (m, 4H), 6.91 (m, 16H), 6.86 (d, 4H), 6.81 (d, 4H), 6.63 (s, 4H), 1.32 (s, 24H).

[Examples 7 and 8] Manufacture of Perovskite Solar Cell

Manufacture of Porous $TiO_2$ Thin Film Substrate

A glass substrate on which a fluorine-containing tin oxide was coated (FTO; F-doped $SnO_2$, 8 ohms/cm$^2$, Pilkington, hereinafter, referred to as FTO substrate (first electrode)) was cut into a size of 25×25 mm, and then an end portion thereof was etched, thereby partially removing FTO.

On the cut and partially etched FTO substrate, a $TiO_2$ dense film having a thickness of 50 nm was prepared by a spray pyrolysis method, as a metal oxide thin film. The spray pyrolysis was carried out using a 20 mM titanium diisopropoxide bis(acetylacetonate) solution (Aldrich), and the thickness was adjusted in a manner of repeating the process of spraying the solution for 3 seconds and stopping spraying for 10 seconds, on the FTO substrate placed on a hotplate maintained at 450° C.

An ethyl cellulose solution in which 10 wt % of ethyl cellulose was dissolved in ethyl alcohol was added to $TiO_2$ powder having an average particle size (diameter) of 50 nm (prepared by hydrothermal treatment of an aqueous titanium peroxocomplex solution in which 1 wt % is dissolved based on $TiO_2$ at 250° C. for 12 hours), at 5 ml per 1 g of $TiO_2$ powder, terpinol was added thereto and mixed at 5 g per 1 g of $TiO_2$ powder, and ethyl alcohol was removed therefrom by distillation under reduced pressure, thereby preparing $TiO_2$ paste.

2-Methoxyethanol was added to the prepared $TiO_2$ powder paste to prepare $TiO_2$ slurry for spin coating. On a $TiO_2$ thin film of the FTO substrate, $TiO_2$ slurry for spin coating was coated by a spin coating method, heat treatment was performed at 500° C. for 60 minutes, then the heat-treated substrate was immersed in a 30 mM $TiCl_4$ aqueous solution at 60° C., stood for 30 minutes, and washed with deionized water and ethanol, dried, and heat-treated again at 500° C. for 30 minutes, thereby preparing a porous $TiO_2$ thin film (porous electron transporter, thickness: 100 nm).

Preparation of Light Absorber Solution

In a 250 ml two-neck round bottom flask, $NH_2CH=NH_2I$ (=FAI) and $CH_3NH_3Br$ (=MABr) were mixed with $PbI_2$ and $PbBr_2$ dissolved in a mixed solution of DMF:DMSO (8:1, v/v), thereby preparing a $(FAPbI_3)_{0.95}(MAPbBr_3)_{0.05}$ perovskite solution having a concentration of 1.05 M.

Preparation of Perovskite Light Absorber

A porous $TiO_2$ thin film substrate (mp-$TiO_2$/bl-$TiO_2$/FTO) prepared above was coated with the light absorber solution prepared above (($(FAPbI_3)_{0.95}(MAPbBr_3)_{0.05}$ perovskite solution) at 1000 rpm for 5 seconds and coated again at 5000 rpm for 1 second, and dried at 150° C. for 10 minutes, thereby preparing a light absorber. Here, 1 mL of diethyl ether was added dropwise to the substrate in the second spin coating step.

Preparation of Hole Conductive Layer Solution for Forming Hole Conductive Layer

In order to form a hole conductive layer, Compound 1 and Compound 2 of Examples 1 and 2 of the present invention were dissolved in chlorobenzene, respectively, to prepare a hole conductor solution having a concentration of 30 mg/ml, and 21.5 μl of Li-bis(trifluoromethanesulfonyl) imide (Li-TFSI)/acetonitrile (170 mg/lml) and 21.5 μl of TBP(4-tert-Butylpyridine) were added thereto as an additive to prepare the hole conductive solution.

Manufacture of Inorganic/Organic Hybrid Perovskite Solar Cell

On composite layer on which the light absorption structure manufactured above was formed on the porous electrode manufactured above, the hole conductive layer solution prepared above was spin-coated at 2000 rpm for 30 minutes, thereby forming a hole conductive layer. Thereafter, on the hole conductive layer, Au was vacuum-deposited by a thermal evaporator under high vacuum ($5 \times 10^{-6}$ torr or less) to form an Au electrode (second electrode) having a thickness of 70 nm, thereby manufacturing a solar cell in the form of Au/(FAPbI$_3$)$_{0.95}$(MAPbBr$_3$)$_{0.05}$(HTM)/mp-TiO$_2$/bl-TiO$_2$/FTO. An active area of the electrode was 0.16 cm$^2$.

The characteristics of the manufactured solar cell are shown in the following Table 1.

Comparative Example 1

A solar cell was manufactured in the same manner as in Examples 7 and 8, except that the following spiro-OMeTAD was used instead of Compound 1 of the hole conductive layer solution, and the characteristics of the manufactured solar cell are shown in the following Table 1.

TABLE 1

| | Hole transport material | Jsc (mA/cm$^2$) | Voc (V) | FF | PCE (%) |
|---|---|---|---|---|---|
| Example 7 | Compound 1 | 24.8 | 1.11 | 81.0 | 22.3 |
| Example 8 | Compound 2 | 24.8 | 1.09 | 80.0 | 21.6 |
| Comparative Example 1 | spiro-OMeTAD | 24.8 | 1.05 | 80.3 | 20.9 |

As shown in Table 1, the solar cell adopting the spirobifluorene compound represented by Chemical Formula 1 of the present invention as the hole transport compound has very high efficiency as compared with the solar cell adopting the conventional hole transport compound.

Specifically, it is recognized that the solar cell adopting the spirobifluorene compound having an amino group substituted with fluorenyl and phenyl of the present invention as the hole transport compound has increased open-circuit voltage (Voc) as compared with the solar cell adopting the spirobifluorene compound having an amino group substituted only phenyl as the hole transport compound, thereby having significantly improved photoelectric transformation efficiency.

<Evaluation of Durability of Solar Cell>

In order to measure the durability of the perovskite solar cells manufactured in Examples 7 and 8, and Comparative Example 1 of the present invention, the solar cells were maintained at a temperature of 60° C. and an average relative humidity of 25 to 30% for 100 hours and 500 hours and the photoelectric transformation efficiency thereof was measured, and this process was performed twice in total.

The results are shown in the following Table 2.

TABLE 2

| | Hole transport material | Photoelectric transformation efficiency (%) as compared with the initial value after 100 hours | Photoelectric transformation efficiency (%) as compared with the initial value after 500 hours |
|---|---|---|---|
| Example 7 | Compound 1 | 98 | 95 |
| Example 8 | Compound 2 | 97 | 96 |
| Comparative Example 1 | spiro-OMeTAD | 86 | 78 |

As seen in Table 2, it is recognized that the photoelectric transformation efficiency of the perovskite solar cells of Examples 7 and 8 of the present invention was not much changed over time and was maintained at 95% of the initial value, while the photoelectric transformation efficiency of Comparative Example 1 was significantly decreased from the initial efficiency and thus, was decreased to 78% of the initial value after 500 hours.

The invention claimed is:

1. A perovskite solar cell comprising a first electrode, an electron transport layer formed over the first electrode, a light absorption layer formed over the electron transport layer, a hole transport layer formed over the light absorption layer, and a second electrode formed over the hole transport layer, wherein the light absorption layer comprises a perovskite compound containing a monovalent organic cation consisting of $R_{21}$-$NH_3^+$ and

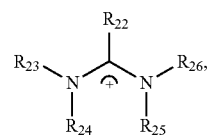

a divalent metal cation, and a halogen anion consisting of BR$^-$ and I$^-$: wherein $R_{21}$ is a C1-C24 alkyl group, a C3-C20 cycloalkyl group, or C6-C20 aryl group, and $R_{22}$ to $R_{26}$ are independently of one another hydrogen, a C1-C24 alkyl group, a C3-C20 cycloalkyl group, or a C6-C20 aryl group, and wherein the hole transport layer comprises a spirobifluorene compound selected from the following compounds:

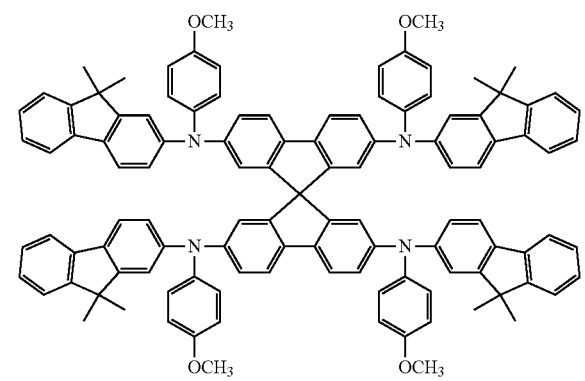

-continued

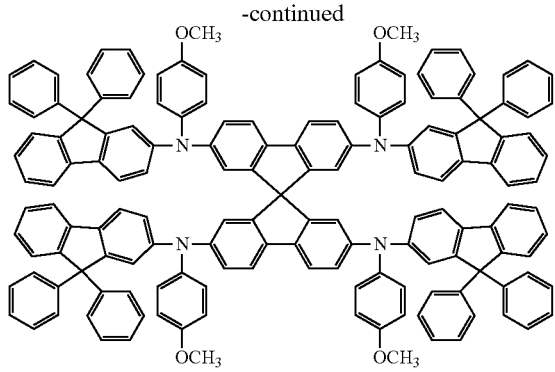

2. A method of making the perovskite solar cell of claim 1, the method comprising:
providing an intermediate structure comprising a first electrode and a light absorption layer over the first electrode, wherein the light absorption layer comprises a perovskite compound containing a monovalent organic cation consisting of $R_{21}$-$NH_3^+$ and

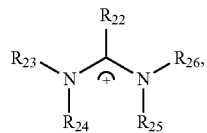

a divalent metal cation, and a halogen anion consisting of $Br^-$ and $I^-$: wherein $R_{21}$ is a C1-C24 alkyl group, a C3-C20 cycloalkyl group, or C6-C20 aryl group, and $R_{22}$ to $R_{26}$ are independently of one another hydrogen, a C1-C24 alkyl group, a C3-C20 cycloalkyl group, or a C6-C20 aryl group;
forming, over the light absorption layer, a hole transport layer comprising a spirobifluorene compound selected from the following compounds:

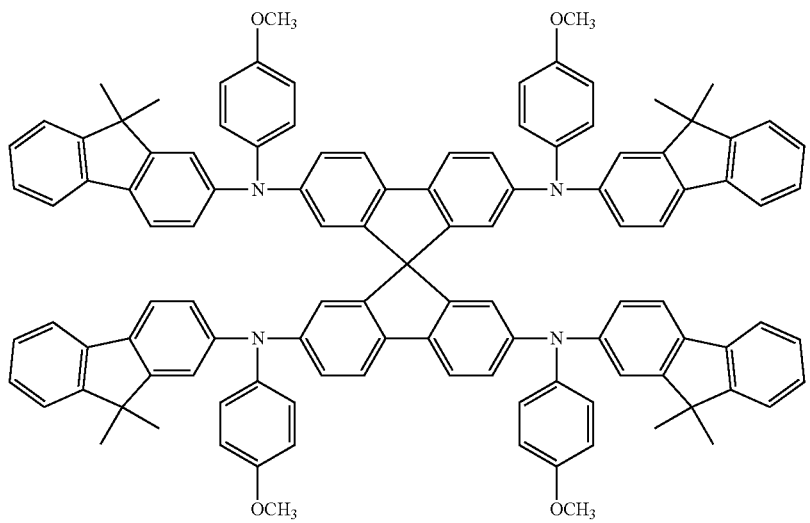

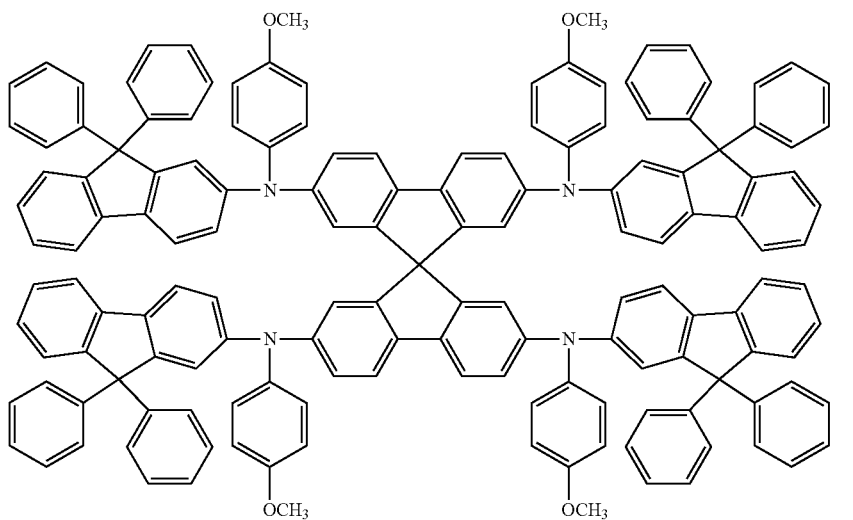

;

and
forming a second electrode over the hole transport layer.

3. The method of claim 2, wherein forming the hole transport layer comprises:
providing a solution comprising the spirobifluorene compound and a solvent;
applying the solution on the surface to form a liquid layer; and
drying the solvent off the liquid layer to form the hole transport layer over the light absorption layer.

* * * * *